(12) United States Patent
Weiman et al.

(10) Patent No.: US 12,016,785 B2
(45) Date of Patent: Jun. 25, 2024

(54) EXPANDABLE INTERVERTEBRAL FUSION DEVICES AND METHODS OF INSTALLATION THEREOF

(71) Applicant: GLOBUS MEDICAL, INC., Audubon, PA (US)

(72) Inventors: Mark Weiman, Downingtown, PA (US); Chad Glerum, Pennsburg, PA (US)

(73) Assignee: GLOBUS MEDICAL INC, Audubon, PA (US)

( * ) Notice: Subject to any disclaimer, the term of this patent is extended or adjusted under 35 U.S.C. 154(b) by 509 days.

(21) Appl. No.: 17/314,464

(22) Filed: May 7, 2021

(65) Prior Publication Data

US 2021/0361443 A1 Nov. 25, 2021

Related U.S. Application Data

(63) Continuation of application No. 16/157,389, filed on Oct. 11, 2018, now Pat. No. 11,013,617, which is a continuation of application No. 14/843,330, filed on Sep. 2, 2015, now Pat. No. 10,137,009.

(51) Int. Cl.
*A61F 2/46* (2006.01)
*A61F 2/44* (2006.01)
*A61F 2/30* (2006.01)

(52) U.S. Cl.
CPC ............ *A61F 2/4611* (2013.01); *A61F 2/447* (2013.01); *A61F 2002/30471* (2013.01); *A61F 2002/30507* (2013.01); *A61F 2002/30538* (2013.01); *A61F 2002/30556* (2013.01); *A61F 2002/30904* (2013.01); *A61F 2002/4627* (2013.01); *A61F 2/4637* (2013.01)

(58) Field of Classification Search
CPC ..................................... A61F 2/44–2002/4698
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Zade Coley

(57) ABSTRACT

Embodiments herein are generally directed to spinal implants, systems, apparatuses, and components thereof that can be used in spinal fusion and/or stabilization procedures, as well as methods of installation. The spinal implants may be expandable. In some embodiments, the spinal implants may be configured to be backfilled with bone graft material after insertion.

18 Claims, 14 Drawing Sheets

(56) References Cited

U.S. PATENT DOCUMENTS

| | | | |
|---|---|---|---|
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 5,980,522 A * | 11/1999 | Koros | A61F 2/446 |
| | | | 606/62 |
| 6,039,761 A | 3/2000 | Li et al. | |
| 6,045,579 A | 4/2000 | Hochschuler et al. | |
| 6,080,193 A | 6/2000 | Hochschuler et al. | |
| 6,099,531 A | 8/2000 | Bonutti | |
| 6,126,689 A | 10/2000 | Brett | |
| 6,176,882 B1 * | 1/2001 | Biedermann | A61F 2/447 |
| | | | 623/17.11 |
| 6,258,125 B1 | 7/2001 | Paul et al. | |
| 6,558,423 B1 | 5/2003 | Michelson | |
| 6,562,074 B2 | 5/2003 | Gerbec et al. | |
| 6,576,016 B1 | 6/2003 | Hochschuler et al. | |
| 6,554,863 B2 | 8/2003 | Paul et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Ulrich | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 7,985,256 B2 | 7/2011 | Grotz et al. | |
| 8,062,375 B2 | 11/2011 | Glerum | |
| 8,070,813 B2 | 12/2011 | Grotz et al. | |
| 8,123,810 B2 | 2/2012 | Gordon | |
| 8,137,405 B2 | 3/2012 | Kostuik et al. | |
| 8,192,495 B2 | 6/2012 | Simpson et al. | |
| 8,303,663 B2 | 11/2012 | Jimenez et al. | |
| 8,353,961 B2 | 1/2013 | McClintock et al. | |
| 8,377,140 B2 | 2/2013 | DeFalco et al. | |
| 8,394,129 B2 | 3/2013 | Lopez et al. | |
| 8,394,143 B2 | 3/2013 | Grotz et al. | |
| 8,398,713 B2 * | 3/2013 | Weiman | A61F 2/44 |
| | | | 623/17.11 |
| 8,435,296 B2 | 5/2013 | Kadaba et al. | |
| 8,454,695 B2 | 6/2013 | Grotz et al. | |
| 8,647,386 B2 | 2/2014 | Gordon | |
| 8,696,751 B2 | 4/2014 | Ashley et al. | |
| 8,771,360 B2 | 7/2014 | Jimenez et al. | |
| 8,845,734 B2 * | 9/2014 | Weiman | A61F 2/4611 |
| | | | 623/17.16 |
| 8,894,710 B2 | 11/2014 | Simpson et al. | |
| 8,932,355 B2 | 1/2015 | Grotz et al. | |
| 8,940,049 B1 | 1/2015 | Jlmenez et al. | |
| 8,956,413 B2 | 2/2015 | Ashley et al. | |
| 8,992,620 B2 | 3/2015 | Ashley et al. | |
| 9,028,550 B2 | 5/2015 | Shulock et al. | |
| 9,358,125 B2 | 6/2016 | Jlmenez et al. | |
| 9,532,883 B2 | 1/2017 | McLuen et al. | |
| 9,603,717 B2 * | 3/2017 | Ibarra | A61F 2/442 |
| 9,622,878 B2 | 4/2017 | Grotz | |
| 2002/0045945 A1 | 4/2002 | Liu | |
| 2002/0068976 A1 | 6/2002 | Jackson | |
| 2002/0068977 A1 | 6/2002 | Jackson | |
| 2003/0176926 A1 | 9/2003 | Boehm et al. | |
| 2004/0030387 A1 | 2/2004 | Landry et al. | |
| 2004/0049271 A1 | 3/2004 | Biedermann | |
| 2004/0054412 A1 | 3/2004 | Gerbec et al. | |
| 2004/0087947 A1 | 5/2004 | Lim et al. | |
| 2004/0088054 A1 | 5/2004 | Berry | |
| 2004/0153065 A1 | 8/2004 | Lim | |
| 2005/0021041 A1 | 1/2005 | Michelson | |
| 2005/0021145 A1 | 1/2005 | de Villiers et al. | |
| 2005/0033432 A1 | 2/2005 | Gordon | |
| 2005/0080422 A1 | 4/2005 | Otte et al. | |
| 2005/0113916 A1 | 5/2005 | Branch | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom et al. | |
| 2006/0058878 A1 | 3/2006 | Michelson | |
| 2006/0084986 A1 | 4/2006 | Grinberg et al. | |
| 2006/0122701 A1 | 6/2006 | Kister | |
| 2006/0129244 A1 | 6/2006 | Ensign | |
| 2006/0142859 A1 | 6/2006 | Mcluen | |
| 2006/0149385 A1 | 7/2006 | Mckay | |
| 2006/0195192 A1 | 8/2006 | Gordon et al. | |
| 2006/0229729 A1 | 10/2006 | Gordon | |
| 2006/0241770 A1 | 10/2006 | Rhoda et al. | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote et al. | |
| 2008/0140207 A1 * | 6/2008 | Olmos | A61F 2/4455 |
| | | | 623/17.11 |
| 2008/0147194 A1 | 6/2008 | Grotz et al. | |
| 2008/0161933 A1 | 7/2008 | Grotz et al. | |
| 2008/0167657 A1 | 7/2008 | Greenhalgh | |
| 2008/0183204 A1 | 7/2008 | Greenhalgh et al. | |
| 2008/0221694 A1 | 9/2008 | Warnick et al. | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac et al. | |
| 2008/0319487 A1 | 12/2008 | Fielding et al. | |
| 2008/0319549 A1 | 12/2008 | Greenhalgh et al. | |
| 2009/0024217 A1 * | 1/2009 | Levy | A61F 2/4455 |
| | | | 623/17.16 |
| 2009/0062833 A1 | 3/2009 | Song | |
| 2009/0076616 A1 | 3/2009 | Duggal et al. | |
| 2009/0125062 A1 | 5/2009 | Amin | |
| 2009/0149956 A1 | 6/2009 | Greenhalgh et al. | |
| 2009/0149959 A1 | 6/2009 | Conner et al. | |
| 2009/0204218 A1 | 8/2009 | Richelsoph | |
| 2009/0222100 A1 | 9/2009 | Cipoletti et al. | |
| 2009/0240334 A1 | 9/2009 | Richelsoph | |
| 2009/0270989 A1 | 10/2009 | Conner et al. | |

(56) References Cited

U.S. PATENT DOCUMENTS

| | | |
|---|---|---|
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1* | 4/2011 | Glerum .......... A61F 2/447 623/17.16 |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1* | 3/2014 | Weiman .......... A61F 2/4611 623/17.16 |
| 2014/0088714 A1 | 3/2014 | Miller et al. |
| 2014/0142701 A1 | 5/2014 | Weiman |
| 2014/0148904 A1 | 5/2014 | Robinson |
| 2014/0163683 A1 | 6/2014 | Seifert et al. |
| 2014/0236296 A1 | 8/2014 | Wagner et al. |
| 2015/0012097 A1* | 1/2015 | Ibarra .......... A61F 2/447 623/17.15 |
| 2015/0066145 A1 | 3/2015 | Rogers et al. |
| 2015/0088258 A1 | 3/2015 | Jimenez et al. |
| 2015/0100128 A1 | 4/2015 | Glerum et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0038305 A1* | 2/2016 | Weiman .......... A61F 2/30767 623/17.16 |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

\* cited by examiner

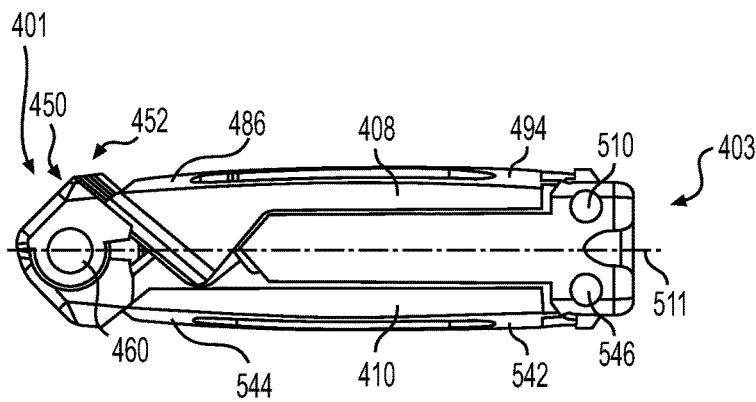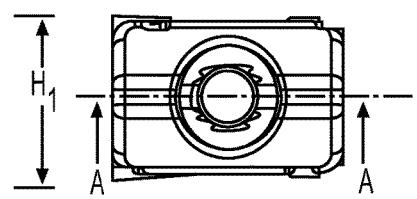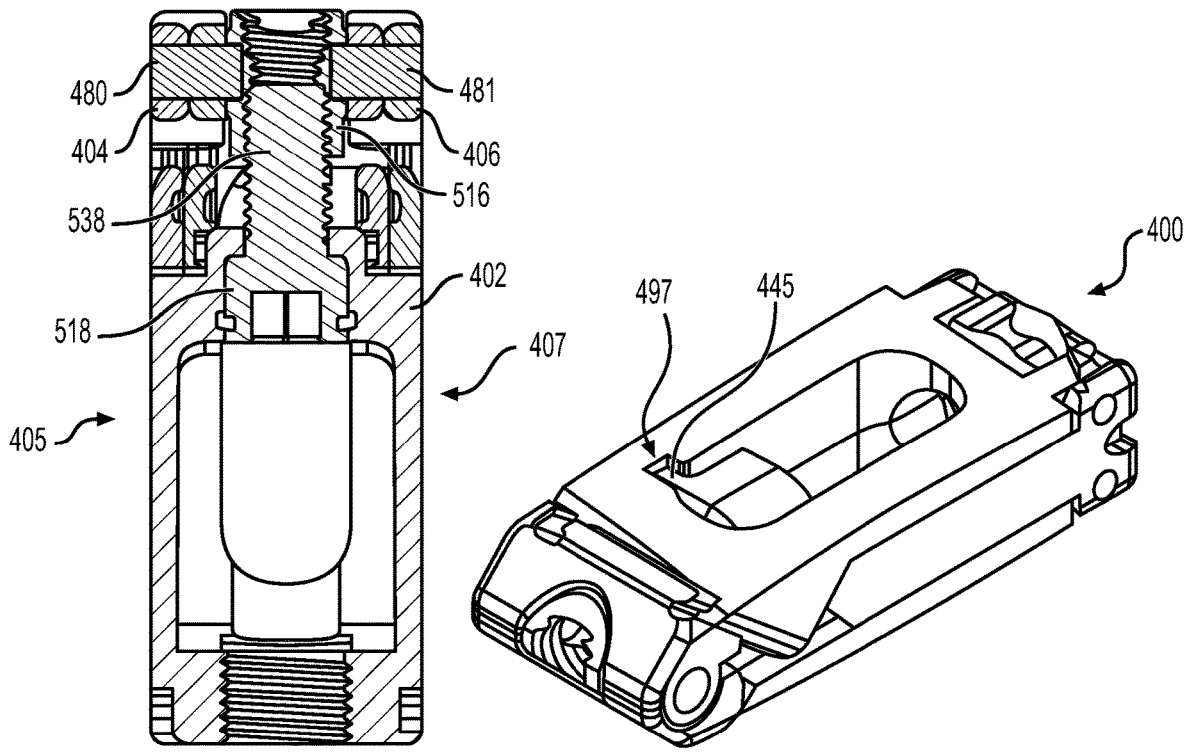
FIG. 16A
FIG. 16B
FIG. 16C
FIG. 16D

EXPANDABLE INTERVERTEBRAL FUSION DEVICES AND METHODS OF INSTALLATION THEREOF

CROSS-REFERENCE TO RELATED APPLICATIONS

This application is a continuation of U.S. patent application Ser. No. 16/157,389, filed on Oct. 11, 2018 (published as U.S. Pat. Pub. No. 2019-0133788), which is a continuation of U.S. patent application Ser. No. 14/843,330, filed on Sep. 2, 2015 (now U.S. Pat. No. 10,137,009), all of which are incorporated herein by reference in their entireties for all purposes.

FIELD OF THE INVENTION

The present disclosure relates to expandable intervertebral devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One example of a spinal irregularity that may result from disc degeneration is spinal stenosis, the narrowing of a spinal canal, which can result in the compression of spinal nerves such as the spinal cord or cauda equina. In turn, the nerve compression can result in pain, numbness, or weakness. Other examples of conditions that can result from disc degeneration are osteoarthritis and disc herniation.

Often, these irregularities can be treated by performing a discectomy and/or immobilizing a portion of the spine. For example, treatment can include a surgical procedure that involves removal and replacement of an affected intervertebral disc with a prosthesis and the subsequent fusion of adjacent vertebrae. The prosthesis, such as an interbody cage or spacer, may be used either alone or in combination with one or more additional devices such as rods, screws, and/or plates.

SUMMARY OF THE INVENTION

Some embodiments herein are directed to an expandable fusion system comprising an expandable spinal implant that can include a body member comprising a first end section, a second end section, and a cavity therebetween, the first end section comprising a first bore and the second end section comprising a second bore; a driving member comprising a tapered section; a first endplate configured to engage the body member and the driving member; a second endplate configured to engage the body member and the driving member; and an actuator assembly comprising an actuation screw, the actuation screw comprising a head and a threaded body, wherein the head is configured to be completely contained between the first endplate and the second endplate.

Other embodiments herein are directed to an expandable fusion system comprising an expandable spinal implant that can include a body member comprising a first end section, a second end section, and a cavity therebetween, the first end section comprising a first bore and the second end section comprising a second bore; a driving member comprising a threaded bore and a tapered outer surface; a first endplate configured to engage the body member and the driving member; a second endplate configured to engage the body member and the driving member; and an actuator assembly comprising an actuation screw, the actuation screw comprising a head and a threaded body, wherein the head is configured to engage the first end section of the body member and the threaded body is configured to engage the threaded bore of the driving member.

Yet other embodiments herein are directed to an expandable fusion system that can include an expandable spinal implant and an inserter, the expandable spinal implant comprising a body member comprising a first end, a second end, and a cavity therebetween, the first end comprising a first bore and the second end comprising a second bore; a driving member comprising a threaded bore and a tapered outer surface; a first endplate configured to engage the body member and the driving member; a second endplate configured to engage the body member and the driving member; an actuator assembly comprising an actuation screw, the actuation screw comprising a head and a threaded body; and the inserter configured to reversibly engage the body member, the inserter comprising a driver configured to be received within the body member and comprising an insertion portion having a length that is equal to at least 35% of a length of the expandable spinal implant.

Some embodiments herein are directed to an expandable fusion system comprising an expandable spinal implant that can include a body member comprising a first end section, a second end section, and a cavity therebetween, the first end section comprising a first bore and the second end section comprising a second bore; a first driving unit; a second driving unit configured to pivot relative to the first driving unit; a first endplate configured to engage the first driving unit; a second endplate configured to engage the second driving unit; and an actuator assembly comprising a nut and an actuation screw.

Other embodiments herein are directed to an expandable fusion system comprising an expandable spinal implant that can include a body member comprising a first end section, a second end section, and a cavity therebetween, the first end section comprising a first bore and the second end section comprising a second bore; a first driving unit; a second driving unit; a first endplate configured to engage the first driving unit and pivot relative to the body member; a second endplate configured to engage the second driving unit and pivot relative to the body member; and an actuator assembly comprising a nut and an actuation screw.

Yet other embodiments herein are directed to an expandable fusion system that can include an expandable spinal implant and an inserter, the expandable spinal implant comprising a body member comprising a first end section, a second end section, and a cavity therebetween, the first end section comprising a first bore and the second end section comprising a second bore; a first driving unit; a second driving unit; a first endplate configured to engage the first driving unit; a second endplate configured to engage the second driving unit; and an actuator assembly comprising a nut and an actuation screw; and an inserter configured to reversibly engage the body member, the inserter comprising a driver configured to be received within the body member and comprising an insertion portion having a length that is equal to at least 35% of a length of the expandable spinal implant.

Further areas of applicability of the present disclosure will become apparent from the detailed description provided hereinafter. It should be understood that the detailed description and specific examples, while indicating certain embodiments, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 16A illustrates a side view of one embodiment of an expandable spinal implant in a collapsed configuration described herein;

FIG. 16B illustrates an end view of one embodiment of an expandable spinal implant in a collapsed configuration described herein;

FIG. 16C illustrates a cross-sectional view of one embodiment of an expandable spinal implant in a collapsed configuration described herein;

FIG. 16D illustrates a perspective view of one embodiment of an expandable spinal implant in a collapsed configuration described herein;

DETAILED DESCRIPTION

Figure 1:
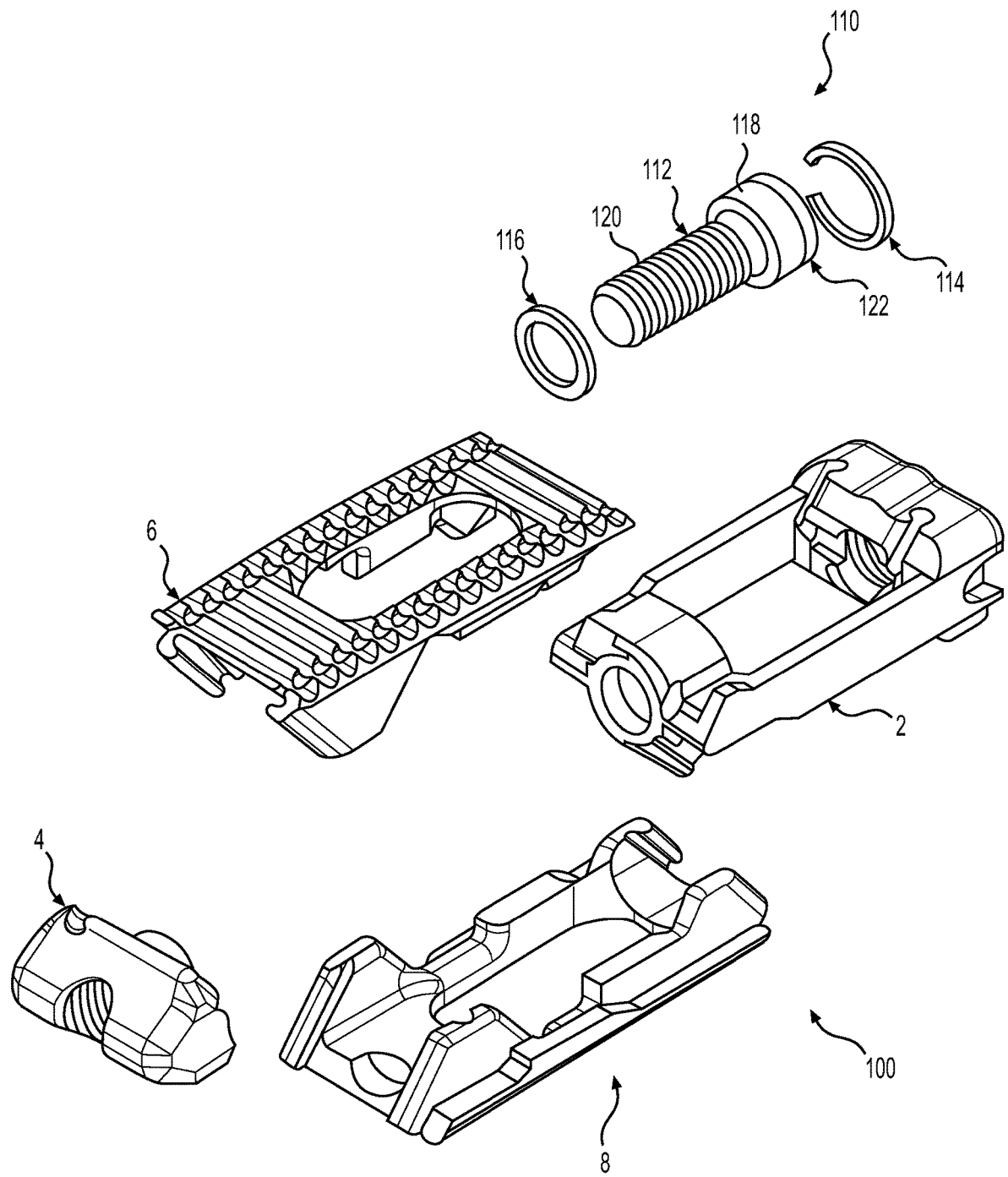
FIG. 1 illustrates an exploded view of one embodiment of an expandable spinal implant described herein.

In a spinal fusion procedure, affected tissue between adjacent vertebrae may be removed and replaced with a prosthesis, such as an interbody cage, spacer, or other spinal implant. The intervertebral disc space can be accessed via various approaches (e.g., anterior, posterior, transforaminal, and/or lateral). To encourage bone growth, the prosthesis may be used in conjunction with bone graft material (e.g., bone chips, demineralized bone matrix, and/or bone morphogenetic proteins). The bone graft material may be packed into hollow areas of the prosthesis. In use, the prosthesis may be designed such that it is pre-packed with bone graft material prior to insertion into the intervertebral space. In contrast, the devices disclosed herein may be advantageously configured to enable backfilling of bone graft material after insertion into the intervertebral space. Those skilled in the art may appreciate that backfilling, rather than pre-filling, the device may enable more bone graft material to be inserted, thereby promoting spinal fusion more effectively. Additionally, the bone graft material may be delivered through the same insertion tool used to insert the device into the intervertebral space. In use, the installation technique of the devices described herein may be simpler and/or more streamlined as compared to other techniques that require a separate tool to deliver bone graft material.

Embodiments herein are directed to spinal implants that may be configured for insertion between adjacent vertebrae for use in, e.g., spinal fusion procedures. The spinal implants may be configured for insertion anywhere along a spinal column, such as between lumbar, thoracic, and/or cervical vertebrae. In some embodiment, the spinal implants described herein may be configured for insertion using a minimally-invasive procedure (e.g., through a cannula). They may be configured for insertion along a variety of approaches, such as transforaminal, posterior, lateral, and/or anterior. For example, in some embodiments, the implants described herein may be configured for insertion at an angle in the range of from about 10° to about 45° relative to a direct posterior approach. In some embodiments, the length of the spinal implant may be in the range of from about 20 mm to about 40 mm. In other embodiments, the width of the spinal implant may be in the range of from about 5 mm to about 20 mm.

Some embodiments herein may be directed to expandable spinal implants. The expandable spinal implants described herein may have a variable height and may be configured to collapse to a smaller height prior to insertion and/or expand to a larger height after insertion. In some embodiments, the expanded height can be from about 25% to about 200% greater than the collapsed height. In other embodiments, the expanded height can be from about 50% to about 100% greater than the collapsed height. In yet other embodiments, the expanded height can be at least about 50% greater than the collapsed height. In some embodiments, the collapsed height can be in the range of from about 5 mm to about 15 mm, and/or the expanded height can be in the range of from about 10 mm to about 20 mm. In other embodiments, the expanded height can be from about 5 mm to about 10 mm greater than the collapsed height.

In some embodiments, the expandable vertebral fusion devices may also have a variable lordotic angle. These devices may include one or more members configured to pivot about a pivot point. These devices may be configured to collapse to a smaller angle (e.g., 15°) prior to insertion and/or expand to a larger angle (e.g., 30°) after insertion. Accordingly, these devices may be configured for use in minimally-invasive surgery (MIS). For example, they may be inserted through a relatively small incision and/or through a cannula, thereby reducing trauma to the patient. Conversely, the expandable vertebral fusion devices described herein may be configured to expand to a height greater than that of other implants in the art, without requiring a larger incision. Furthermore, the height and/or lordotic angle of the expandable vertebral fusion devices may be adjusted after insertion, thereby providing a customized fit within the intervertebral space.

Components of all of the devices and systems disclosed herein can be made of materials known to those skilled in the art, including metals (e.g., titanium), metal alloys (e.g., stainless steel, titanium alloys, and/or cobalt-chromium alloys), ceramics, polymers (e.g., poly ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. In some embodiments, the systems and devices may include radiolucent and/or radiopaque materials. In other embodiments, one or more components may be coated with a bone growth-enhancing material, such as hydroxyapatite. The components can also be machined and/or manufactured using techniques known to those skilled in the art. For example, polymeric components may be injection-molded or blow-molded. Additionally, the devices disclosed herein may be used together with materials that encourage bone growth, such as bone graft material, demineralized bone matrix, bone chips, and/or bone morphogenetic proteins. In some embodiments, these materials may advantageously be packed into hollow areas of the devices described herein.

As described herein, the spinal implants of the present disclosure may be configured for placement between two adjacent vertebrae, for example, as part of a spinal fusion procedure. These spinal implants may be referred to as, without limitation, interbody spacers, interbody fusion devices, vertebral fusion devices, interbody cages, and/or intervertebral cages. Each of the spinal implants described herein may include a superior and/or inferior surface (e.g., on the endplates described herein) that is configured to engage and/or contact a vertebral endplate or other vertebral surface. In some embodiments, the superior and/or inferior surfaces may be convex, corresponding to the topography of the vertebral surface. Accordingly, in some embodiments, the superior and/or inferior surfaces may be curved along a path that is offset from a longitudinal and/or transverse axis thereof. Additionally, the superior and/or inferior surfaces of each of the spinal implants described herein may include one or more texturizing members. Examples of such texturizing members include, but are not limited to, projections, bumps, teeth, grooves, peaks, spikes, and/or knurling. These texturizing features may advantageously enhance the interaction or fiction, and/or reduce movement, between the implant and the vertebrae.

Those skilled in the art may appreciate that directional terms such as "anterior," "posterior," "superior," "inferior," "leading," "trailing," "top," "bottom," and the like may be used herein for descriptive purposes and do not limit the orientation(s) in which the devices may be used. For example, those skilled in the art may appreciate that, in use, a "superior" surface may be installed adjacent an inferior vertebra, and vice versa. Accordingly, a feature described as being on top may actually be oriented towards the bottom after installation.

Figure 2:
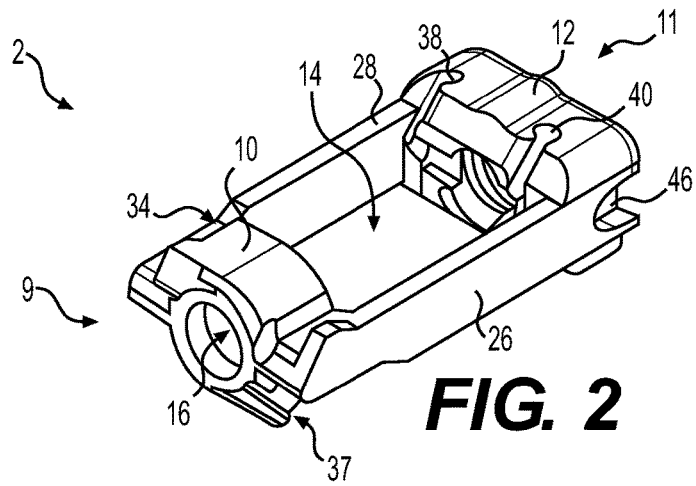
FIG. 2 illustrates a perspective view of one embodiment of a body member described herein.

Turning now to FIGS. 1-9C, some embodiments herein are directed to an expandable fusion system that can include an expandable spinal implant 100. As illustrated in FIG. 8C, the expandable spinal implant 100 can include a first end 3, a second end 5, a first side 7, and a second side 9. As illustrated in FIG. 1, the expandable spinal implant 100 can include a body member 2, a driving member 4, a first endplate 6, and/or a second endplate 8. As illustrated in FIG. 2, the body member 2 can include a first end 9 having a first end section 10, and a second end 11 having a second end section 12. The body member 2 can also include a cavity 14 between the first and second end sections 10, 12. In some embodiments, the first end section 10 may be referred to as the leading and/or distal end section. The second end section 12 may be referred to as the trailing and/or proximal end section.

Figure 3A:
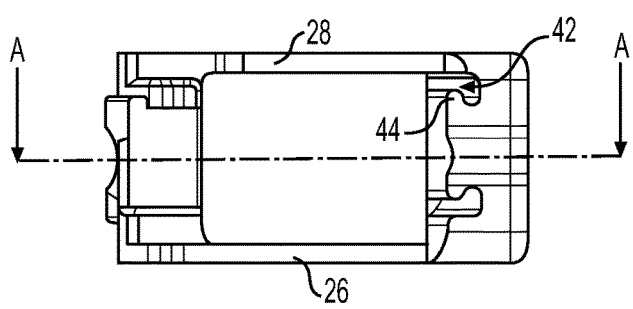
FIG. 3A illustrates a top view of one embodiment of a body member described herein.
Figure 3B:
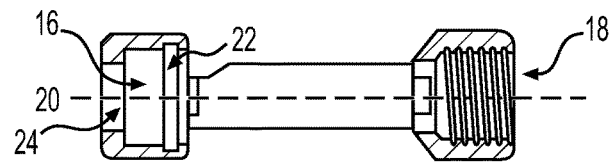
FIG. 3B illustrates a cross-sectional view of one embodiment of a body member described herein.
Figure 3C:
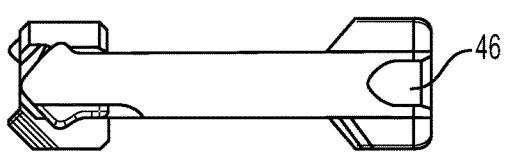
FIG. 3C illustrates a side view of one embodiment of a body member described herein.

As illustrated in FIG. 3B, the first end section 10 can include a first bore 16 and the second end section 12 can include a second bore 18. The first and second bores 16, 18 can define an elongate channel extending longitudinally through the body member 2. As illustrated in FIG. 3B, the first and second bores 16, 18 can be coaxial along longitudinal axis 20 of the body member 2. The first bore 16 may be non-threaded (e.g., smooth). In some embodiments, it can include a circumferential groove 22. The first bore 16 can have a constant or variable diameter. In some embodiments, the first bore 16 can include a first section having a first diameter and a second section having a second diameter that is different than the first diameter. For example, the first bore 16 can include a reduced-diameter section 24 located at the first end 9 of the body member 2. The second bore 18 may be threaded. The second bore 18 may be configured to threadably engage an insertion tool (e.g., inserter 200) as described further herein. The second bore 18 may also be configured to receive bone graft material therethrough.

Figure 3D:
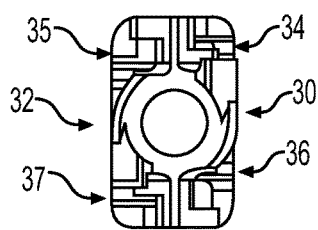
FIGS. 3D-E illustrate end views of one embodiment of a body member described herein.
Figure 3E:
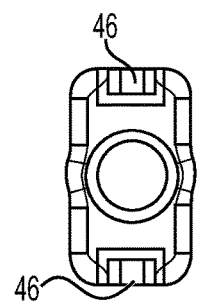
Figure 4:
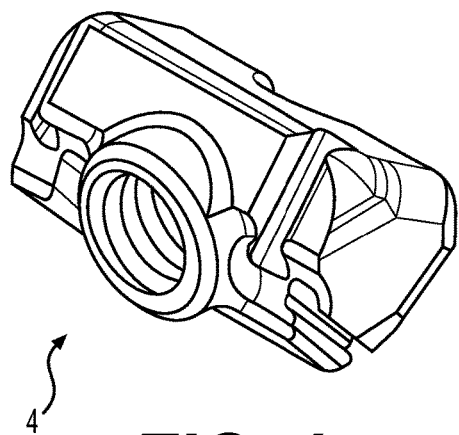
FIG. 4 illustrates a perspective view of one embodiment of a driving member described herein.

As illustrated in FIGS. 2 and 3A, the body member 2 can also include a first side wall 26 and a second side wall 28. Each of the first and second side walls 26, 28 can extend from the first end section 10 to the second end section 12. As illustrated in FIG. 3A, the cavity 14 can be defined between and/or bounded by the first end section 10, second end section 12, first side wall 26, and second side wall 28. The second end section 12 can also include one or more tool-engagement feature(s) 46, such as a notch, cut-out, or groove. Each tool-engagement feature 46 may be configured to engage an insertion tool (e.g., outer sleeve 202) as described further herein. In some embodiments, the body member 2 can include two or more tool-engagement features 46. As illustrated in FIG. 3E, the body member 2 can include a first tool-engagement feature on the first side wall 26 and a second tool-engagement feature on the second side wall 28.

The body member 2 can include one or more mating elements. Each of the mating elements may be configured (e.g., shaped) to mate with a complementary mating element on the first and/or second endplates 6, 8, as described herein. As illustrated in FIG. 3D, the body member 2 (e.g., first end section 10 and/or second end section 12) can include at least a first mating element at a third (e.g., top and/or superior) side 30 and at least a second mating element at a fourth (e.g., bottom and/or inferior) side 32. The first mating element can be configured to engage the first endplate 6 and the second mating element can be configured to engage the second endplate 8. In some embodiments, the first end section 10 can include two mating elements 34, 36 at the third side 30 and two mating elements 35, 37 at the fourth side 32. The second end section 12 can include two mating elements 38, 40 at the third side 30, illustrated in FIG. 2, and two mating elements (not shown) at the fourth side 32. Each mating element can be ramped (e.g., angled, inclined, and/or declined), and/or can include a ramped member. In some embodiments, one or more mating elements on the body member 2 can include a protrusion (e.g., a tongue, rail, and/or shoulder). In other embodiments, one or more mating elements on the body member 2 can include a recess (e.g., a groove, track, and/or channel). In some embodiments, the mating element can include an extension member. For example, as illustrated in FIG. 3A, mating element 38 can include a groove 42 and an extension tab 44 that can at least partially protrude into the groove. Those skilled in the art may appreciate the groove 42 may be configured to receive a portion of a mating element of the first endplate 6 therein. Additionally, the tab 44 may provide enhanced engagement with the first endplate 6 thereby reducing movement, separation, and/or decoupling between the first endplate 6 and body member 2 when in use. As illustrated in FIG. 2, mating elements 34, 38, and/or 40 may include a groove and a tab. In other embodiments, any and/or all mating elements of the body member 2 can include a groove and a tab. In yet other embodiments, the mating element can include a protrusion and an engagement receptacle that overlaps the protrusion.

As described further herein, each mating element may have substantially similar inclinations, when in an assembled configuration, as their corresponding complementary mating elements on the first and/or second endplates 6, 8. In some embodiments, each mating element on the third side 30 (e.g., mating elements 34, 36, 38, and/or 40) can be inclined longitudinally from the first end 9 towards the second end 11 of the body member 2. In other embodiments, each mating element on the fourth side 32 can be declined longitudinally from the first end 9 towards the second end 11 of the body member 2. In other embodiments, the mating elements on the third side and the mating elements on the fourth side may diverge from each other along longitudinal axis 20 from a position relatively adjacent to the first end 9 to a position relatively adjacent to the second end 11. In yet other embodiments, the mating elements on the body member 2 may be angled away from the longitudinal axis 20, e.g., towards the second end 11.

Figure 5A:
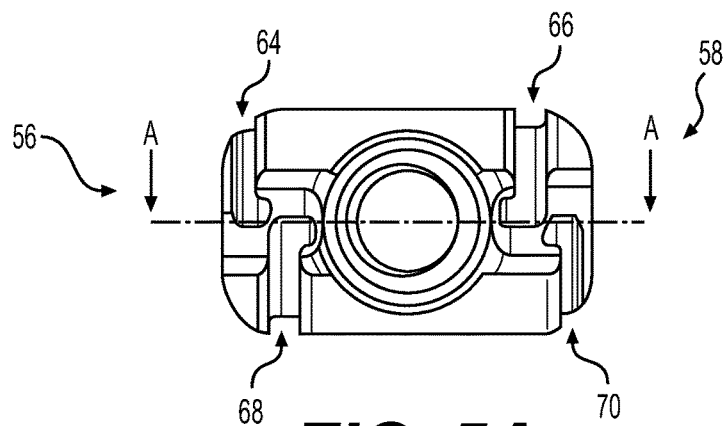
FIG. 5A illustrates an end view of one embodiment of a driving member described herein.
Figure 5B:
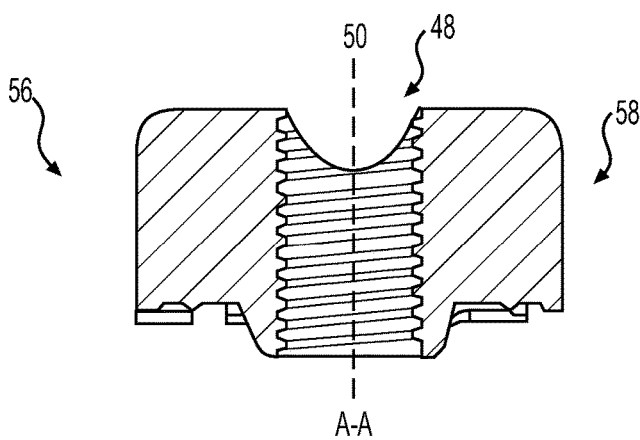
FIG. 5B illustrates a cross-sectional view of one embodiment of a driving member described herein.
Figure 5C:
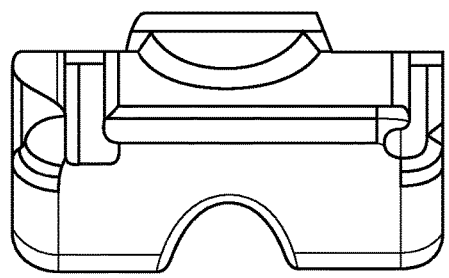
FIG. 5C illustrates a top view of one embodiment of a driving member described herein.
Figure 5D:
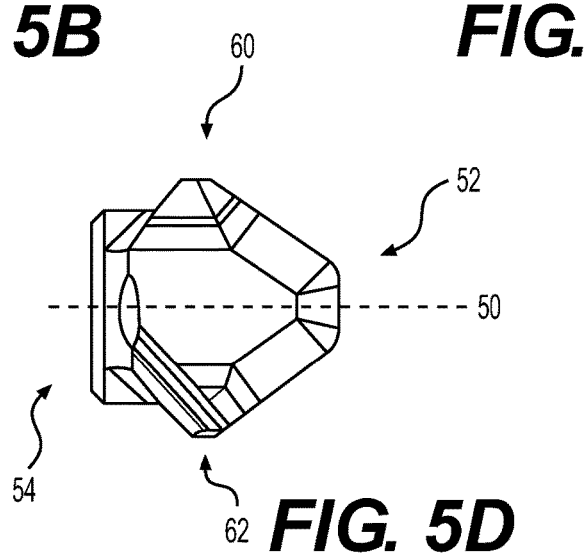
FIG. 5D illustrates a side view of one embodiment of a driving member described herein.
Figure 8A:
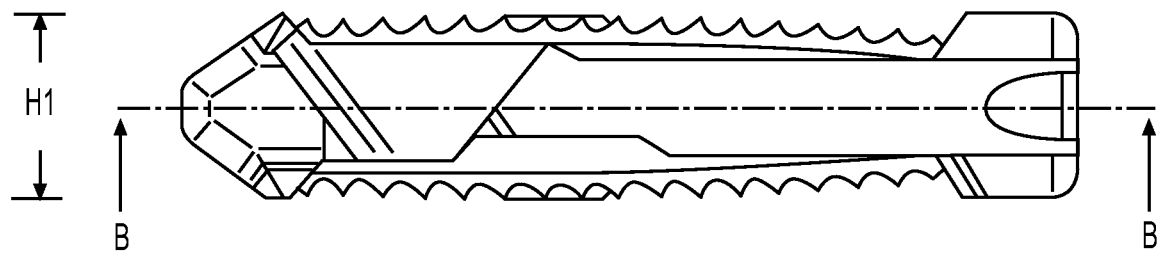
FIG. 8A illustrates a side view of one embodiment of an expandable spinal implant in a collapsed configuration described herein.
Figure 8B:
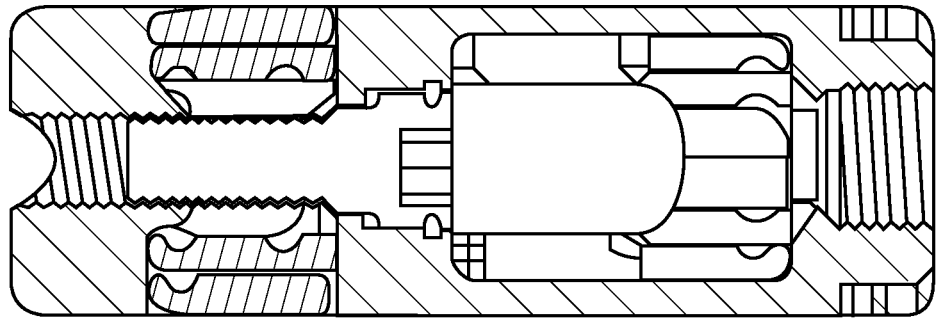
FIG. 8B illustrates a cross-sectional view of one embodiment of an expandable spinal implant in a collapsed configuration described herein.
Figure 8C:
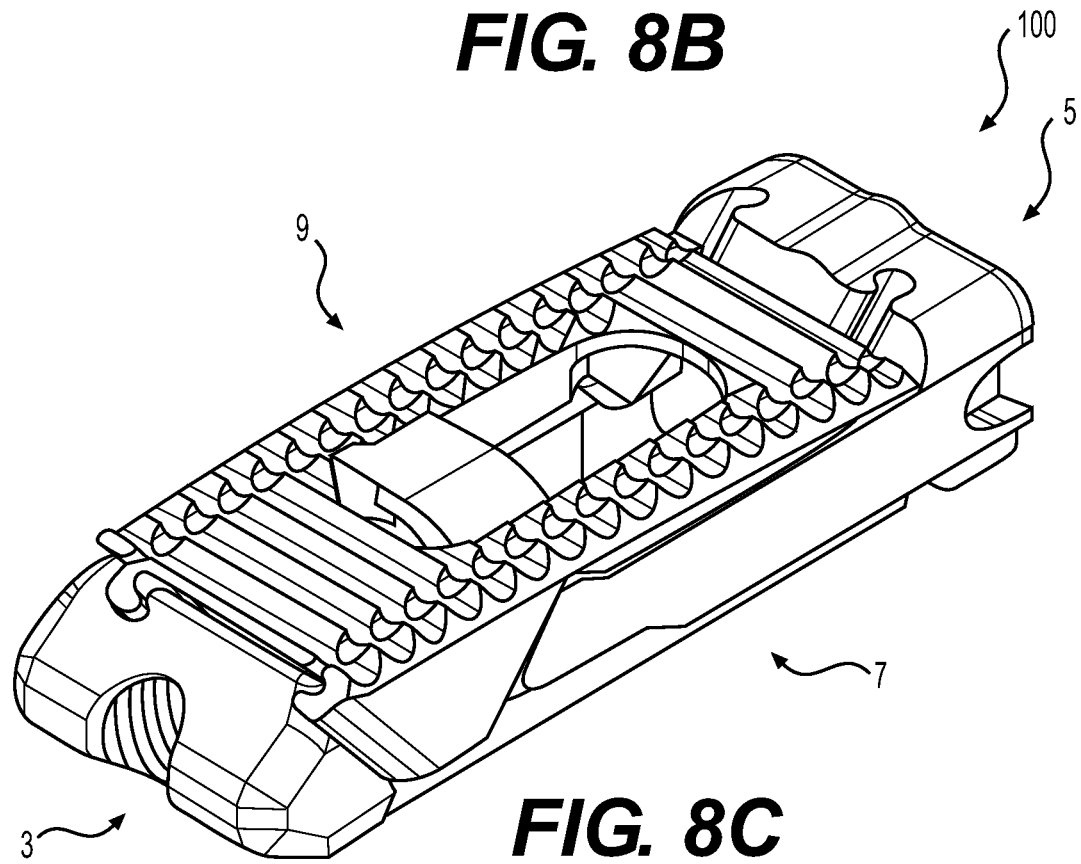
FIG. 8C illustrates a perspective view of one embodiment of an expandable spinal implant in a collapsed configuration described herein.

The driving member 4 can be configured to engage the first and/or second endplates 6, 8. When in an assembled configuration, the driving member 4 can be located distal to the body member 2 (e.g., closer to the first end 9 than the second end 11), as illustrated in FIGS. 8A-C. The driving member 4 can include a first (e.g., leading and/or distal) end 52 and a second (e.g., trailing and/or proximal) end 54, as illustrated in FIG. 5D. As illustrated in FIGS. 5B and 5D, the driving member 4 can also include a first side 56, a second side 58, a third (e.g., top and/or superior) side 60, and a fourth (e.g., bottom and/or inferior) side 62. The driving member 4 can include a width that is generally equal to a width of the body member 2. The driving member 4 can include a tapered section. The tapered section may be located at the first end 52 of the driving member 4. The tapered section can have a variable height. For example, as illustrated in FIG. 5D, at least a portion of the driving member 4 can have a height that decreases towards the first end 52. As illustrated in FIG. 5B, the driving member 4 can include a single bore, such as central threaded bore 48. The bore 48 may extend longitudinally through the driving member 4. The bore 48 may be coaxial with a central longitudinal axis 50 of the driving member. When in an assembled configuration, the bore 48 can be coaxial with the first and/or second bores 16, 18 of the body member 2. The bore 48 may be configured to threadably engage the threaded body of the actuation screw 112 as described further herein.

The driving member 4 can include one or more mating elements. The mating element(s) can be generally located at the second end 54 of the driving member 4. In some embodiments, the driving member 4 can include at least one mating element at (e.g., extending from and/or adjacent to) the third side 60 and at least one mating element at (e.g., extending from and/or adjacent to) the fourth side 62. Those skilled in the art may appreciate that the mating element(s) at the third side 60 may be configured to engage the first endplate 6 and the mating element(s) at the fourth side 62 may be configured to engage the second endplate 8. In other embodiments, the driving member 4 can include at least one mating element at the first side 56 and at least one mating element at the second side 58. As illustrated in FIG. 5A, the second end 54 can include first mating element 64, second mating element 68, third mating element 66, and fourth mating element 70. The first and third mating elements 64, 66 may be located at the third side 60. Mating element 64 may be adjacent to the first side 56 and mating element 66 may be adjacent to the second side 58 of the driving member 4. The second and fourth mating elements 68, 70 may be located at the fourth side 62. Mating element 68 may be adjacent to the first side 56 and mating element 70 may be adjacent to the second side 58 of the driving member 4.

Each mating element can be configured (e.g., shaped) to mate with a complementary mating element on the first and/or second endplates 6, 8 as described herein. The mating elements on the driving member 4 can include some or all of the features of the mating elements on the body member 2. Each mating element can be ramped (e.g., angled, inclined, and/or declined), and/or can include a ramped member. In some embodiments, one or more mating elements on the driving member 4 can include a protrusion (e.g., a tongue, rail, and/or shoulder). In other embodiments, one or more mating elements on the driving member 4 can include a recess (e.g., a groove, track, and/or channel). In some embodiments, one or more mating elements can include a groove and a tab that can at least partially protrude into the groove, as described herein with respect to the body member 2. Those skilled in the art may appreciate the groove may be configured to receive a tab of a mating element of the first and/or second endplates 6, 8. The tab may provide enhanced engagement with the first endplate 6 thereby reducing movement, separation, and/or decoupling between the first endplate 6 and body member 2 when in use.

As described further herein, each mating element of the driving member 4 may have substantially similar inclinations, when in an assembled configuration, as their corresponding complementary mating elements on the first and/or second endplates 6, 8. In some embodiments, each mating element on the third side 60 (e.g., mating elements 64 and/or 66) can be inclined longitudinally from the second end 54 towards the first end 52 of the driving member 4. In other embodiments, each mating element on the fourth side 62 can be declined longitudinally from the second end 54 towards the first end 52 of the driving member 4. In other embodiments, the mating elements on the third side 60 and the mating elements on the fourth side 62 may diverge from each other along longitudinal axis 50 from a position relatively adjacent to the second end 54 to a position relatively adjacent to the first end 52. In yet other embodiments, the mating elements on the driving member 4 may be angled relative to the longitudinal axis 50, e.g., towards the first end 52.

The first and/or second endplates 6, 8 may be configured to engage the body member 2 and the driving member 4. In use, the expandable implant 100 may be oriented such that the first endplate 6 is the top, superior, and/or upper endplate and the second endplate 8 is the bottom, inferior, and/or lower endplate. First endplate 6 and second endplate 8 may include some or all of the same features. Those skilled in the art may appreciate that the description of the first endplate 6 herein may be applied to the second endplate 8 unless stated otherwise.

Figure 6A:
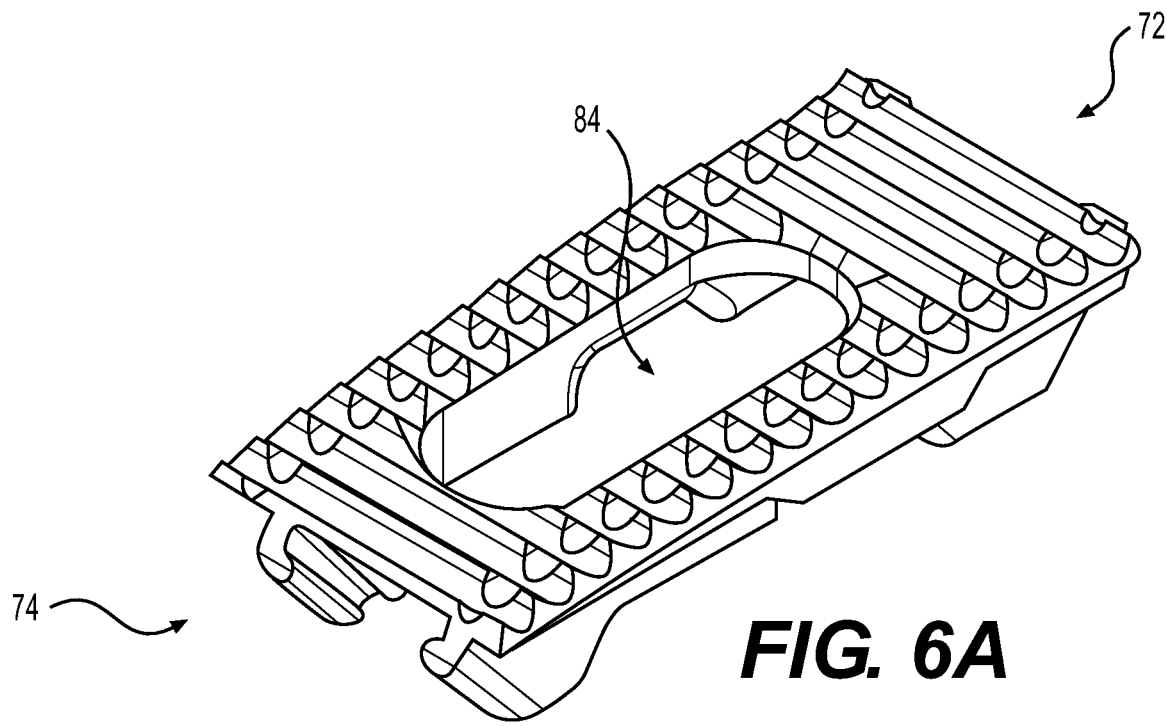
FIGS. 6A-B illustrate perspective views of one embodiment of an endplate described herein.
Figure 7A:
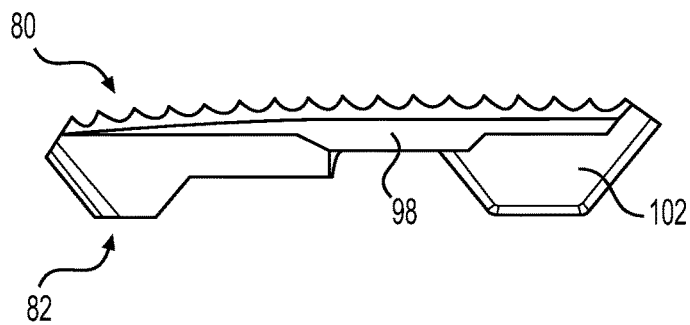
FIG. 7A illustrates a side view of one embodiment of an endplate described herein.
Figure 7B:
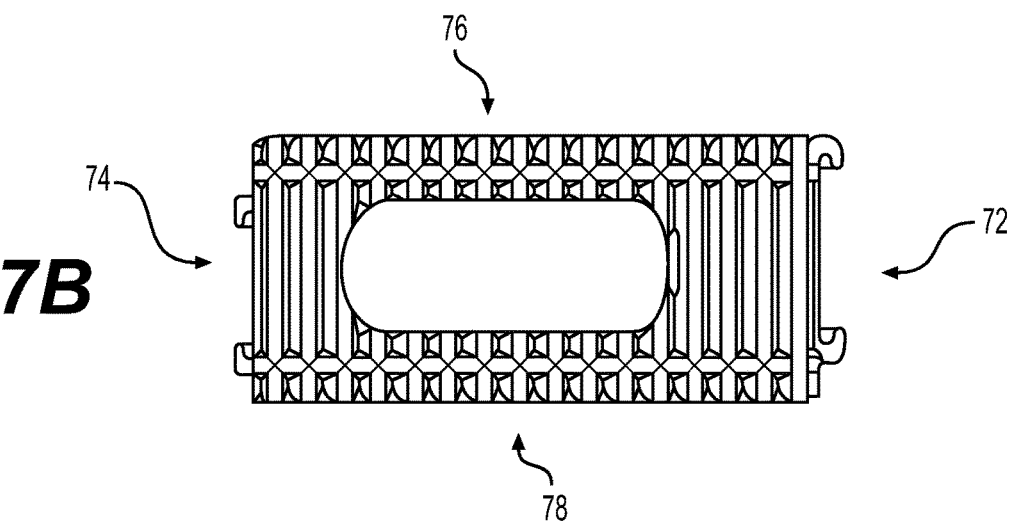
FIG. 7B illustrates an outer view of one embodiment of an endplate described herein.
Figure 7C:
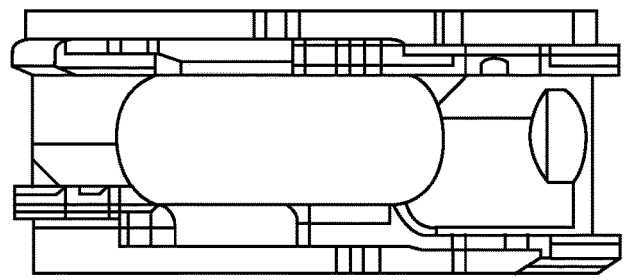
FIG. 7C illustrates an inner view of one embodiment of an endplate described herein.

First endplate 6 can be configured to slideably and/or movably engage the body member 2 and/or the driving member 4. As illustrated in FIG. 7B, first endplate 6 can include a first (e.g., leading and/or distal) end 72, a second (e.g., trailing and/or proximal) end 74, a first side 76, and a second side 78. The first endplate 6 can include a length between the first and second ends 72, 74, and a width between the first and second sides 76, 78. As illustrated in FIG. 7A, the first endplate 6 can also include a third (e.g., outer) side 80 and a fourth (e.g., inner) side 82. As illustrated in FIG. 6A, the first endplate 6 can also include a through-hole 84 that passes from the outer side 80 to the inner side 82. The through-hole 84 can be configured to enable bone graft material deposited within the expandable implant 100 to engage, contact, and/or fuse with an adjacent vertebral body. The outer side 80 may be configured to engage a vertebral body. The outer side 80 may be referred to as an outer surface and/or a superior surface. As illustrated in FIG. 7B, the outer side 80 can include a plurality of protrusions (e.g., bumps, teeth, and/or peaks) configured to retain the implant 100 within an intervertebral space. The outer side 80 can be generally planar, concave, and/or convex.

Figure 6B:
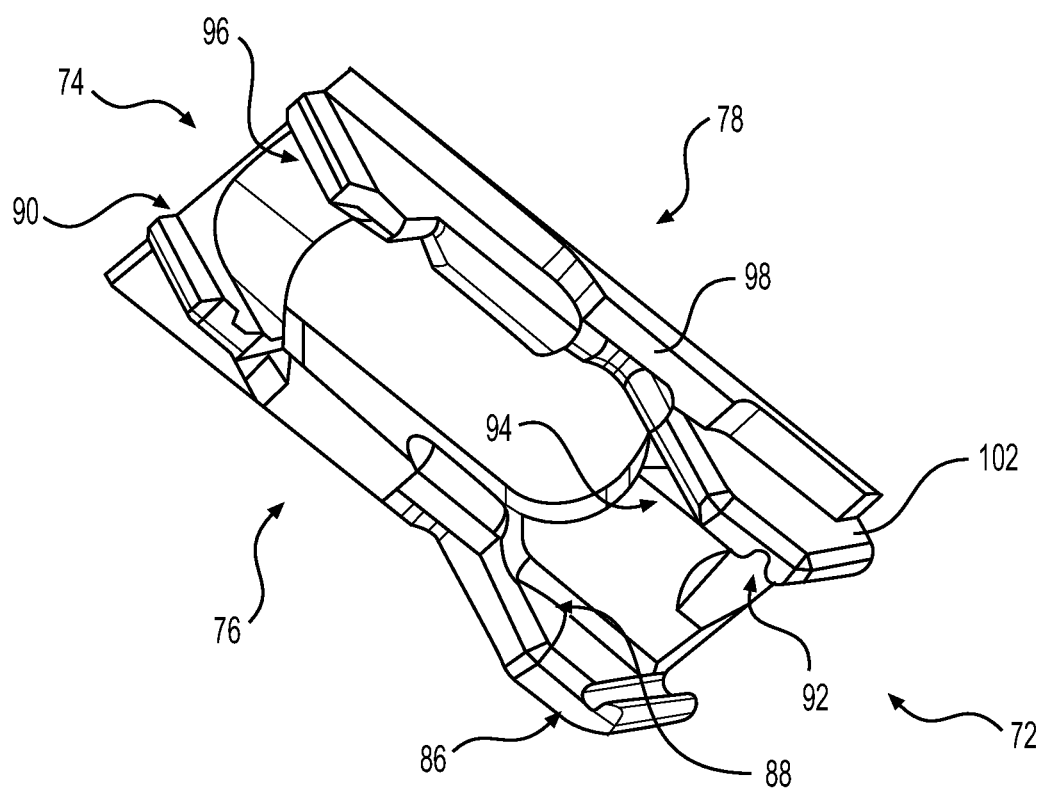
Figure 7D:
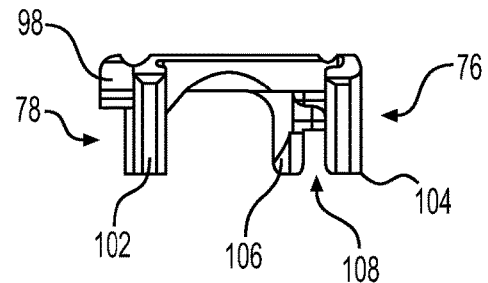
FIG. 7D illustrates an end view of one embodiment of an endplate described herein.

In some embodiments, inner side 82 can include at least one wall segment extending therefrom. Each wall segment may extend partially or completely along the length of the first endplate 6. As illustrated in FIG. 6B, the first side 76 can include at least one wall segment and the second side 78 can include at least one wall segment. In some embodiments, the first side 76 and/or the second side 78 can include a plurality of overlapping and/or staggered wall segments. The wall segments may be staggered along the length and/or width of the first endplate 6. For example, as illustrated in FIGS. 7A and 7D, the second side 78 can include an outer wall segment 98 and an inner wall segment 102. As illustrated in FIG. 7D, the first side 76 can include an outer wall segment 104 and an inner wall segment 106 separated by a gap 108. The overlapping and/or staggered wall segments can advantageously enable the first and second endplates 6, 8 to overlap, thereby reducing the height of the expandable implant 100 when in a collapsed configuration, for example, as illustrated in FIGS. 8A-C.

The first endplate 6 can include one or more mating elements. In some embodiments, one or more mating elements of the first endplate 6 can include a protrusion (e.g., a tongue, rail, and/or shoulder). In other embodiments, one or more mating elements of the first endplate 6 can include a recess (e.g., a groove, track, and/or channel). In some embodiments, at least one mating element can include an extension member. For example, at least one of the mating elements can a groove and an extension tab that can at least partially protrude into the groove. As another example, the mating element can include a protrusion and an engagement receptacle that overlaps the protrusion. The mating element(s) on the first endplate 6 can be configured to form a slidable joint with complementary mating element(s) on the body member 2 and/or the driving member 4. Accordingly, the body member 2 and/or the driving member 4 may be configured to slideably engage the first endplate 6. The slideable joint may advantageously enable the expandable implant 100 to transition reversibly between expanded and contracted configurations. The slidable joint may include, for example, a tabled splice joint, a dovetail joint, a tongue and groove joint, or another suitable joint. In some embodiments, one or more mating elements on the first endplate 6 can include a recess (e.g., a groove, track, and/or channel), and one or more mating elements on the body member 2 and/or the driving member 4 can include a protrusion (e.g., a tongue, rail, and/or shoulder) configured to slide within the groove. In other embodiments, one or more mating elements on the first endplate 6 can include a protrusion and one or more mating elements on the body member 2 and/or the driving member 4 can include a recess.

In some embodiments, the mating elements may be located on and/or extend from the inner side 82. In some embodiments, at least one mating element may be located on a wall segment. In other embodiments, the first side 76 can include at least one mating element and the second side 78 can include at least one mating element. In yet other embodiments, the first and/or second sides 76, 78 can each include a mating element at the first end 72, a mating element at an intermediate portion, and a mating element at the second end 74. As illustrated in FIG. 6B, the first endplate 6 can include a first mating element 86, a second mating element 88, a third mating element 90, a fourth mating element 92, a fifth mating element 94, and/or a sixth mating element 96. The first, second, and third mating elements 86, 88, 90 may be located at the first side 76 and the fourth, fifth, and sixth mating elements 92, 94, 96 may be located at the second side 78 of the first endplate 6. Furthermore, the first and/or fourth mating elements 86, 92 may be adjacent to the first end 72 of the first endplate 6, the second and/or fifth mating elements 88, 94 may be adjacent to the intermediate portion of the first endplate 6, and the third and/or sixth mating elements 90, 96 may be adjacent to the second end 74 of the first endplate 6. The mating elements on the first side 76 can be separated from corresponding mating elements on the second side 78 by a distance (e.g., width). In some embodiments, each mating element on the first side 76 may be separated from a complementary mating element on the second side 78 by the same distance. In other embodiments, for example, as illustrated in FIG. 6B, the third and sixth mating elements 90, 96 may be separated by a distance that is less than the distance separating the first and fourth mating elements 86, 92 and/or the second and fifth mating elements 88, 94.

The first and fourth mating elements 86, 92 may each be configured to engage a complementary mating element on the driving member 4. The other mating elements may each be configured to engage a complementary mating element on the body member 2. Accordingly, each mating element can be ramped (e.g., angled, inclined, and/or declined), and/or can include a ramped member. The mating elements on the first endplate 6 may have substantially similar inclinations, when in an assembled configuration, as their corresponding complementary mating elements on the driving member 4 and/or body member 2. As illustrated in FIG. 6B, first and fourth mating elements 86, 92 of the first endplate 6 may be angled (e.g., inclined or declined) away from the outer side 80 in a direction from the first end 72 towards the second end 74. The second, third, fifth, and/or sixth mating elements 88, 90, 94, 96 of the first endplate 6 may be angled (e.g., inclined or declined) away from the outer side 80 in a direction from the second end 74 towards the first end 72 (e.g., in a direction opposite the first and/or fourth mating elements 86, 92). Those skilled in the art may appreciate, for example, that the first and second mating elements 86, 88 may be angled in opposing directions and/or may extend along intersecting axes. In contrast, the second and third mating elements 88, 90 may extend along generally parallel axes.

As illustrated in FIG. 1, the expandable spinal implant 100 can include an actuator assembly 110. The actuator assembly 110 can include an actuation screw 112. In some embodiments, the actuator assembly 110 can also include a snap ring 114 and/or a washer 116. The actuation screw 112 can include a head 118 and a threaded body 120. The head 118 can be configured to be completely contained between the first and second endplates 6, 8 when the expandable spinal implant 100 is in an assembled configuration, as illustrated in FIGS. 8A-9C. The head 118 may be configured to engage the first end section 10 of the body member 2. For example, the head 118 can be configured to be received within the first bore 16 of the body member 2. In some embodiments, the head 118 can include a diameter that is greater than a diameter of the reduced-diameter section 24 of the first bore. The threaded body 120 can include an outer diameter that is less than the diameter of the reduced-diameter section 24. The threaded body 120 can be configured to engage the driving member 4. For example, the threaded body 120 may be configured to threadably engage the central threaded bore 48 of the driving member 4. The head 118 can include a tool-engagement feature, such as a recess or socket. The tool-engagement feature may be configured to engage a driver as described herein. As illustrated in FIG. 1, the head 118 can include a circumferential groove 122. The circumferential groove 122 can be configured to receive the snap ring 114 therein. The circumferential groove 122 of the actuation screw 112 may be longitudinally aligned with the circumferential groove 22 of the body member 2. Accordingly, both circumferential grooves 22, 122 may be configured to receive at least a portion of the snap ring 114 therein. Those skilled in the art may appreciate that in use, the snap ring 114 may advantageously retain the actuation screw 112 within the body member 2. The washer 116 may have an outer diameter generally less than or equal to the diameter of the first bore 16, and may have an inner diameter generally greater than or equal to the diameter of the reduced-diameter section 24 of the first bore 16. The washer 116 may be configured to receive the threaded body 120 of the actuation screw 112 therethrough. The washer 116 may be configured to be received within the first bore 16 of the body member 2. In use, the washer 116 may be positioned between the head 118 of the actuation screw 112 and the body member 2, and may advantageously provide a bearing surface for the actuation screw 112.

Figure 9A:
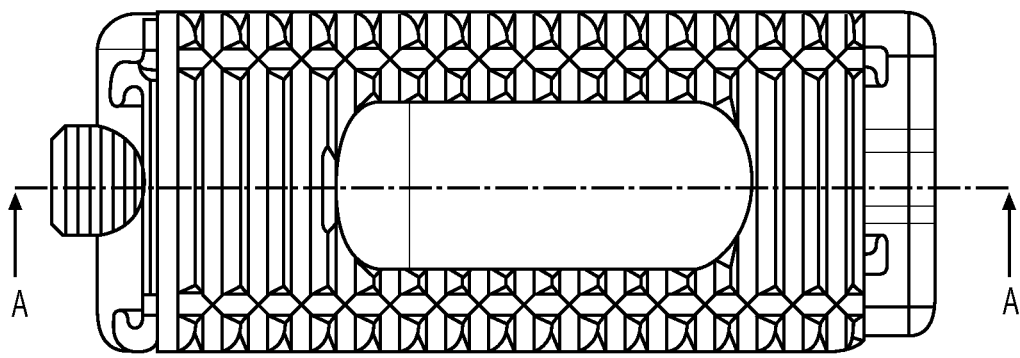
FIG. 9A illustrates a side view of one embodiment of an expandable spinal implant in an expanded configuration described herein.
Figure 9B:
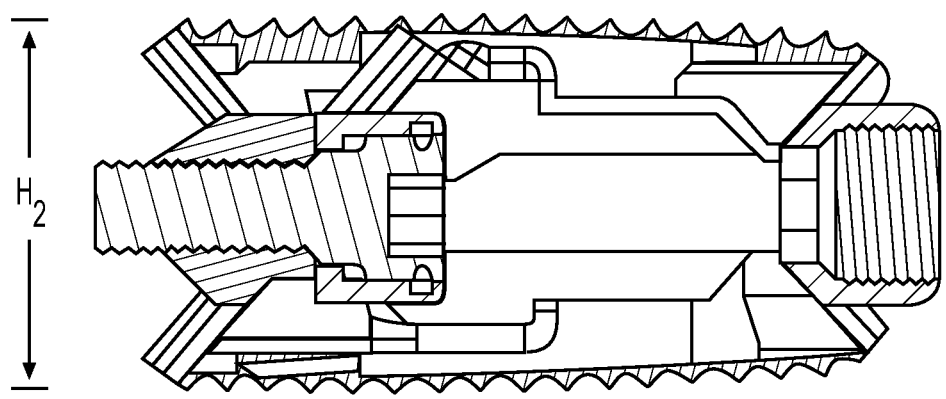
FIG. 9B illustrates a cross-sectional view of one embodiment of an expandable spinal implant in an expanded configuration described herein.
Figure 9C:
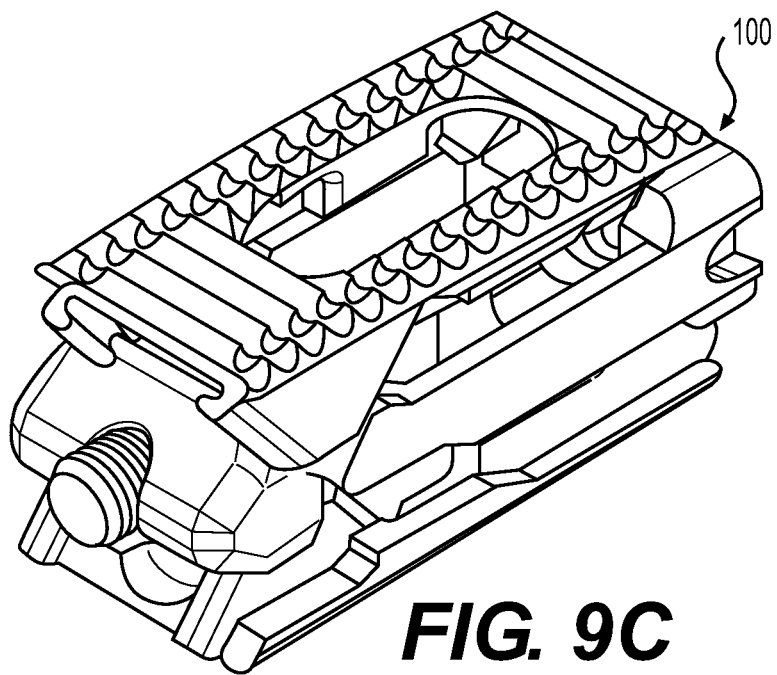
FIG. 9C illustrates a perspective view of one embodiment of an expandable spinal implant in an expanded configuration described herein.

In use, the expandable spinal implant 100 may advantageously be configured to reversibly transition between a collapsed configuration and an expanded configuration. In the collapsed configuration, for example, as illustrated in FIGS. 8A-C, the expandable spinal implant 100 can include a first height Hi (e.g., as measured from the outer surface of the first endplate 6 to the outer surface of the second endplate 8). In the expanded configuration, for example, as illustrated in FIGS. 9A-C, the expandable spinal implant 100 can include a second height, $H_2$, that is greater than the first height. In some embodiments, the second height can be from about 25% to about 200% greater than the first height. In other embodiments, the second height can be from about 50% to about 100% greater than the first height. In other embodiments, the second height can be from at least about 50% greater than the first height. In some embodiments, the first height can be in the range of from about 5 mm to about 15 mm, and/or the second height can be in the range of from about 10 mm to about 20 mm. In other embodiments, the second height can be from about 5 mm to about 10 mm greater than the first height. In some embodiments, the change in height can be caused by movement of the first and second endplates 6, 8 towards and/or away from each other. In these embodiments, the first and second endplates 6, 8 can be separated by a first distance when in the collapsed configuration and a second distance when in the expanded configuration, wherein the second distance is greater than the first distance. In some embodiments, the implant 100 may be wedge-shaped when in the collapsed and/or expanded configurations. For example, the first end 3 may have a height that is different from a height of the second end 5, and/or the first end 7 may have a height that is different from a height of the second side 9. Advantageously, this shape can enhance contact between the implant 100 and vertebral endplates, thereby encouraging a secure fit within an intervertebral space. Those skilled in the art may appreciate that, in use, the height of the expandable spinal implant 100 can be adjusted to accommodate an individual patient's anatomy. Additionally, the expandable spinal implant 100 may be inserted into an intervertebral space in the collapsed configuration, which may entail less trauma to surrounding tissue due to its smaller size.

Some embodiments herein are directed to an expandable fusion system that can include an expandable spinal implant as described herein (e.g., expandable spinal implant 100 and/or 400) and an inserter 200 as illustrated in FIGS. 10A-D. The inserter 200 can be configured to reversibly engage at least a portion of the expandable spinal implant (e.g., the body member 2 of the expandable spinal implant 100). In FIGS. 10A-D, the inserter 200 is illustrated as being engaged with expandable spinal implant 100. However, those skilled in the art may appreciate that in other embodiments, the inserter 200 may be similarly engaged with spinal implant 400, described further herein.

Figure 10A:
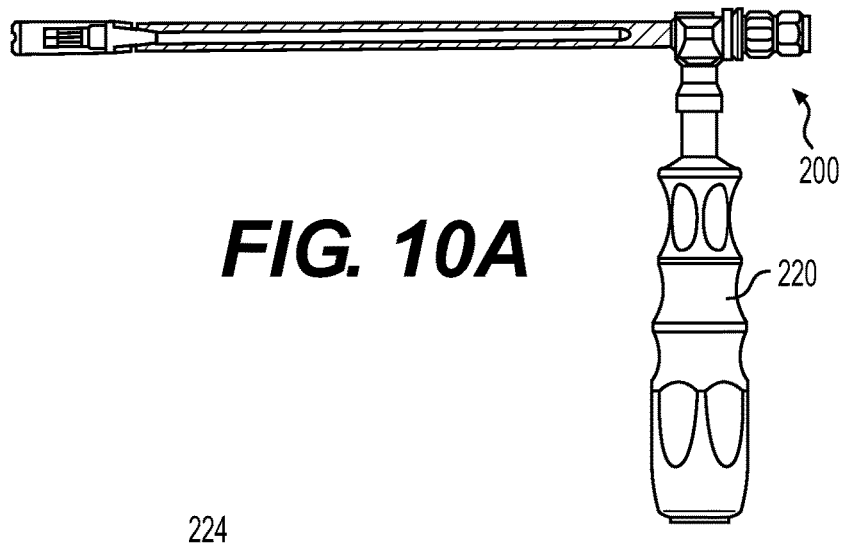
FIG. 10A illustrates a side view of one embodiment of an expandable fusion system described herein.
Figure 10B:
FIGS. 10B-C illustrate cross-sectional views of one embodiment of an expandable fusion system described herein.
Figure 10C:
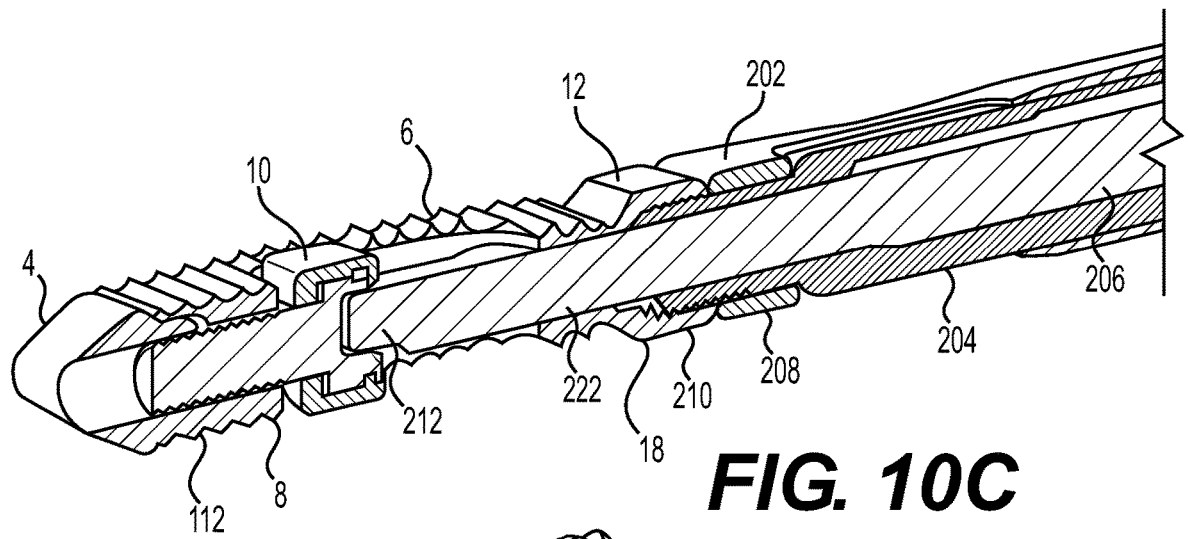

As illustrated in FIG. 10C, the inserter 200 can include an outer sleeve 202, an inner sleeve 204, and/or a driver 206. The inserter 200 can also include a handle member 220. The handle member 220 may be rotatably and/or pivotably coupled to the outer sleeve 202. The outer and/or inner sleeves 202, 204 can each include a cannula extending longitudinally therethrough between a first (e.g., distal) end and a second (e.g., proximal) end. As illustrated in FIG. 10B, each cannula can include a first opening at a first (e.g., distal) end 216 of the inserter 200 and a second opening at a second (e.g., proximal) end 218 of the inserter 200. The cannula of the inner sleeve 204 may be configured to reversibly receive the driver 206 therethrough. The driver 206 may be configured to rotate within the cannula of the inner sleeve 204. The cannula of the outer sleeve 202 may be configured to reversibly receive the inner sleeve 204 therethrough. The inner sleeve 204 may be configured to rotate within the outer sleeve 202. When in an assembled configuration, the outer sleeve 202, inner sleeve 204, and driver 206 may be coaxial.

Figure 10D:
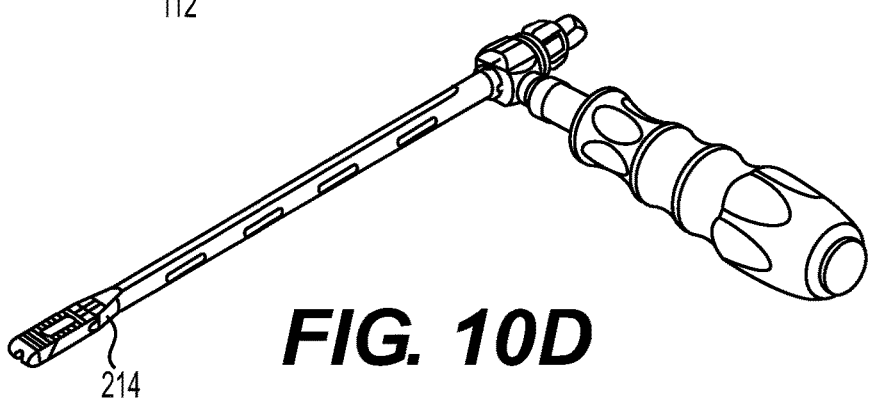
FIG. 10D illustrates a perspective view of one embodiment of an expandable fusion system described herein.

As illustrated in FIG. 10C, the outer sleeve 202 can include a first end 208 that can be configured to engage the body member of the expandable implant (e.g., body member 2). As illustrated in FIG. 10D, the first end 208 can include at least one countertorque tab 214 extending distally therefrom. In some embodiments, the first end 208 can include two countertorque tabs 214. Each countertorque tab 214 can be configured to engage one of the tool-engagement features of the body member (e.g., tool-engagement feature 46). In use, the countertorque tab(s) 214 may reduce, inhibit, and/or prevent relative motion between the inserter 200 and the expandable implant 100.

As illustrated in FIG. 10C, the inner sleeve 204 can include a first end 210 that can include exterior threading. At least a portion of the first end 210 can be configured to be received within the expandable spinal implant. For example, the exterior threads on the inner sleeve 204 can be configured to threadably engage the second bore 18 of the body member 2. In use, the inner sleeve 204 can be configured to couple the inserter 200 to the expandable spinal implant.

As illustrated in FIG. 10B, the driver 206 can include a first end 224 and a second end 226. The driver 206 can include a length that is greater than a length of the outer and/or inner sleeves 202, 204. For example, the first end 224 and/or the second end 226 can extend outside the inner and/or outer sleeves 202, 204. As illustrated in FIG. 10C, the first end 224 of the driver 206 can include an insertion portion 222 configured to be received within the body member of the expandable spinal implant. In some embodiments, the insertion portion 222 can have a length in the range of from 10% to about 80% of the length of the expandable implant. In other embodiments, the insertion portion 222 can have a length in the range of from about 20% to about 60% of the length of the expandable implant. In yet other embodiments, the insertion portion 222 can have a length that is equal to at least 35% of a length of the expandable implant. In other embodiments, the insertion portion 222 can have a length that is equal to at least 50% of a length of the expandable implant. As illustrated in FIG. 10C, the insertion portion can include a tip 212 that can be configured to engage the actuation screw (e.g., actuation screw 112). In some embodiments, the tip 212 can be at least partially received within the tool-engagement feature of the head (e.g., screw head 118).

Embodiments herein are also directed to methods of installing the expandable spinal implant 100. Methods can include providing the expandable spinal implant 100 in the collapsed configuration as described herein. Methods can also include coupling the expandable spinal implant 100 with inserter 200. This step can include inserting the countertorque tab(s) 214 of the inserter 200 into the tool-engagement feature(s) 46 of the body member 2. This step can also include threading the first end 210 of the inner sleeve 204 of the inserter 200 into the second bore 18 of the body member 2. Those skilled in the art may appreciate that in other embodiments, the spinal implant 100 may be installed without the use of the inserter 200.

In some embodiments, the method can also include inserting the expandable spinal implant 100 between two adjacent vertebrae. Those skilled in the art may appreciate that the first end 52 of the driving member 4 may define the leading end of the implant 100. Accordingly, the tapered first end 52 may advantageously be used to distract the adjacent vertebrae. As described herein, the expandable spinal implant 100 may be inserted anywhere along the spinal column, such as between lumbar, thoracic, and/or cervical vertebrae. In addition, the expandable spinal implant 100 may be inserted along any approach, such as transforaminal, posterior, lateral, and/or anterior. In some embodiments, the implant 100 may be inserted using minimally invasive methods. In some embodiments, the intervertebral space may be prepared beforehand, for example, by performing a discectomy to remove some or all of the intervertebral disc.

The method can also include expanding the expandable implant 100, for example, by transitioning the implant 100 from the collapsed configuration to the expanded configuration. To expand the implant 100, the driving member 4 may be moved towards the body member 2, or vice versa. This step can include urging a driver into engagement with the actuation screw 112. In some embodiments, this step can include inserting driver 206 through the inner sleeve 204 and/or the body member 2 and into engagement with the actuation screw 112, as illustrated in FIG. 10C. In these embodiments, the inner sleeve 204 may be coupled with the expandable implant 100 prior to engaging the driver 206 with the actuation screw 112. For example, as illustrated in FIG. 10C, the first end 210 of the inner sleeve 204 may threadably engage the second bore 18 of the body member 2.

Once the driver is engaged with the actuation screw 112, the step of expanding the implant 100 can also include applying a rotational force to the driver 206 to rotate the actuation screw 112. As the actuation screw 112 rotates in a first direction, the threaded body 120 engages the driving member 4, translating the driving member 4 relative to the body member 2. As the body member 2 and the driving member 4 translate towards each other, the respective mating elements of the body member 2 and/or the driving member 4 may push against corresponding complementary mating elements on the first and second endplates 6, 8, thereby pushing the first and second endplates 6, 8 apart and increasing the height of the implant 100. In other embodiments, as the actuation screw 112 is rotated in a second direction, the threaded body 120 may push the driving member 4 away from the body member 2, or vice versa. Thus, those skilled in the art may appreciate that the implant 100 may be reversibly expandable and/or collapsible. Accordingly, some embodiments can include reducing and/or adjusting the height of the implant 100, for example, by bringing the first and second endplates 2, 4 together. In some embodiments, the implant 100 can include a locking member configured to lock the implant in the collapsed and/or expanded configuration. In these embodiments, the method can also include the step of locking the implant 100 at a particular height.

After the expandable implant 100 has been expanded, the driver 206 may be removed (e.g., may be pulled proximally through the cannula of the inner sleeve 204). Bone graft material may then be inserted into the cavity 14 of the body member 2. In some embodiments, the bone graft material may be inserted through the cannula of the inner sleeve 204 to the cavity 14. Advantageously, the implant 100 may be backfilled with bone graft material in situ, rather than being prepacked prior to insertion. Accordingly, more bone graft material can be inserted, thereby promoting increased fusion. Additionally, the same cannula (e.g, of the inner sleeve 204) may be used to insert the driver 206 and the bone graft material. Advantageously, this method may save time and/or materials as compared to other methods that rely on separate instruments for insertion (and/or expansion) of the implant and subsequent insertion of bone graft material.

Figure 11:
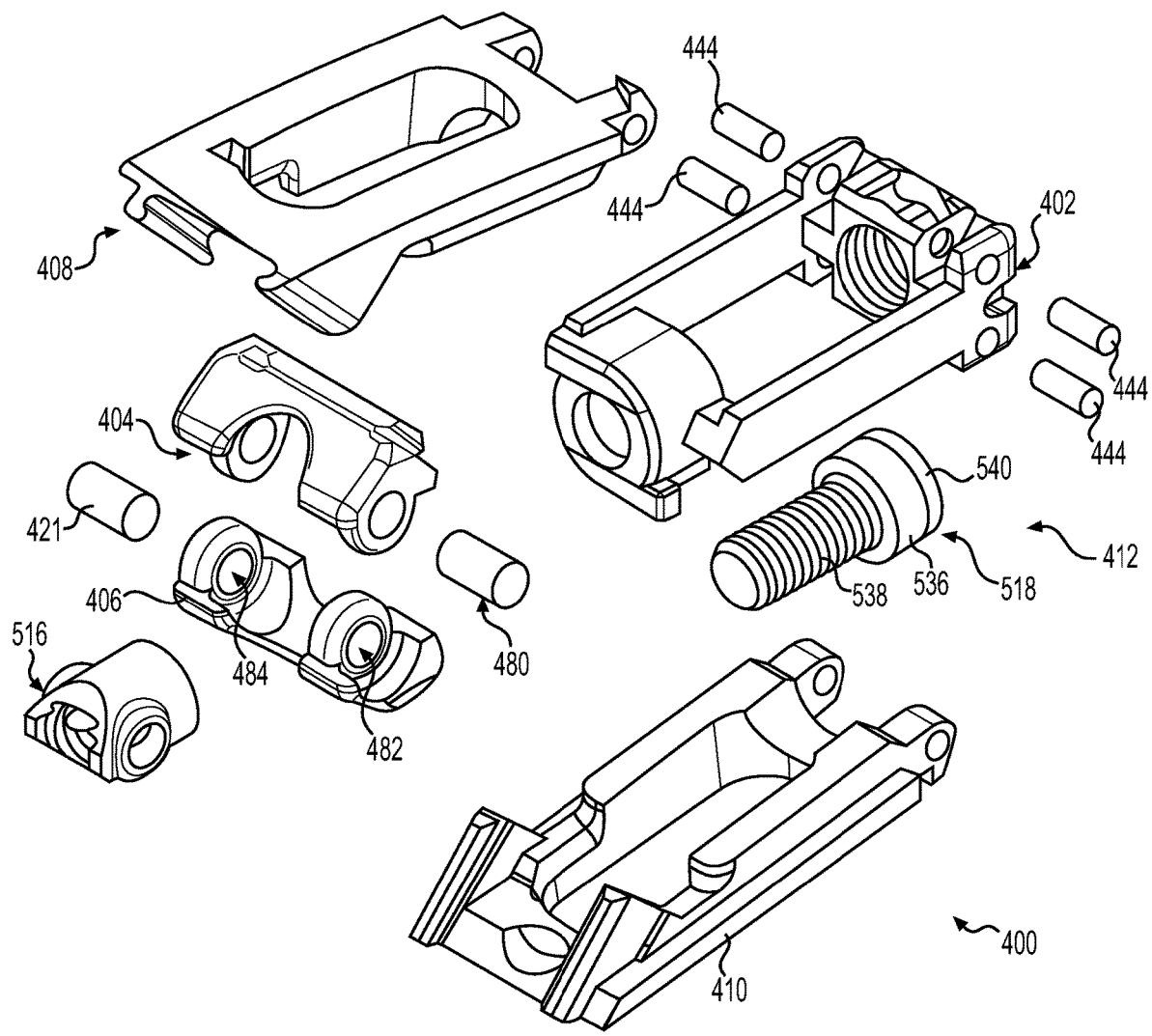
FIG. 11 illustrates an exploded view of one embodiment of an expandable spinal implant described herein.

Turning now to FIGS. 11-17D, an alternative embodiment of an expandable spinal implant is illustrated. As illustrated in FIG. 11, expandable spinal implant 400 can include a body member 402, a first (e.g., upper and/or superior) driving unit 404, a second (e.g., lower and/or inferior) driving unit 406, a first (e.g., upper and/or superior) endplate 408, a second (e.g., lower and/or inferior) endplate 410, and an actuator assembly 412. As illustrated in FIG. 16A, the expandable spinal implant 400 can also include a first (e.g., leading and/or distal) end 401 and a second (e.g., trailing and/or proximal) end 403. As illustrated in FIG. 16C, the expandable spinal implant 400 can include a first (e.g., anterior) side 403 and a second (e.g., posterior) side 405. As described further herein, expandable spinal implant 400 can include an adjustable height and/or lordotic angle. In some embodiments, the expandable spinal implant 400 may be configured to pivotably expand. As described further herein, the first and/or second endplates 408, 410 may be configured to pivot relative to the body member 402. In some embodiments, the expandable spinal implant 400 may be part of an expandable fusion system, for example, in combination with the inserter 200.

Figure 12A:
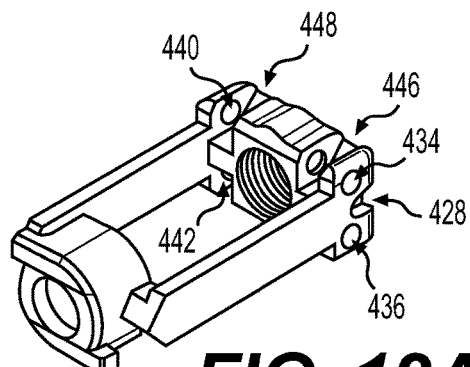
FIG. 12A illustrates a perspective view of one embodiment of a body member described herein.
Figure 12B:
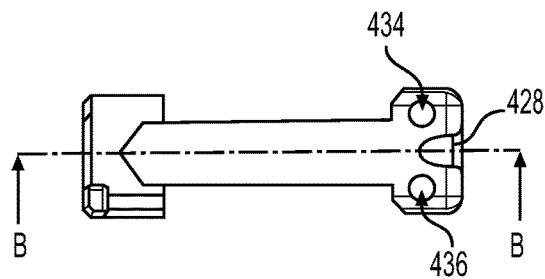
FIG. 12B illustrates a side view of one embodiment of a body member described herein.
Figure 12C:
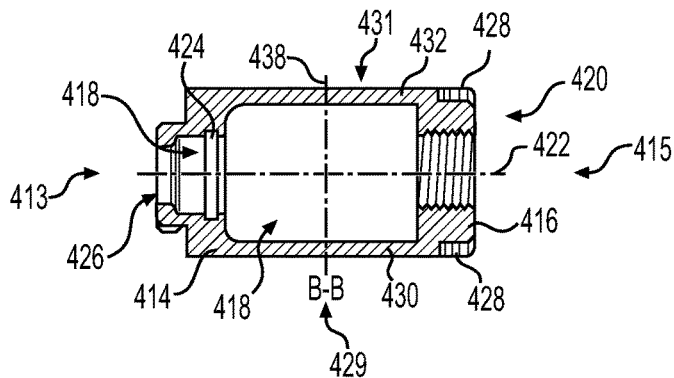
FIG. 12C illustrates a cross-sectional view of one embodiment of a body member described herein.

As illustrated in FIG. 12C, the body member 402 can include a first end 413 having a first end section 414 and a second end 415 having a second end section 416. The body member 402 can also include a cavity 418 between the first and second end sections 414, 416. In some embodiments, the first end 413 may be referred to as the leading and/or distal end. The second end 415 may be referred to as the trailing and/or proximal end.

As illustrated in FIG. 12C, the first end section 414 can include a first bore 418 and the second end section 416 can include a second bore 420. The first and second bores 418, 420 can define an elongate channel extending longitudinally through the body member 402. As illustrated in FIG. 12C, the first and second bores 418, 420 can be coaxial along longitudinal axis 422 of the body member 402. The first bore 418 may be non-threaded (e.g., smooth). In some embodiments, it can include a circumferential groove 424. The first bore 418 can have a constant or variable diameter. In some embodiments, the first bore 418 can include a first section having a first diameter and a second section having a second diameter that is different than the first diameter. For example, the first bore 418 can include a reduced-diameter section 426 located at the first end 413 of the body member 402. The reduced-diameter section 426 may be a distal section of the first bore 418. The second bore 420 may be threaded. The second bore 420 may be configured to threadably engage an insertion tool as described further herein. The second bore 420 may also be configured to receive bone graft material therethrough.

As illustrated in FIG. 12C, the body member 402 can also include a first side wall 430 at a first side 429 and a second side wall 432 at a second side 431. Each of the first and second side walls 430, 432 can extend from the first end section 414 to the second end section 416. As illustrated in FIG. 12C, the cavity 418 can be defined between and/or bounded by the first end section 414, second end section 416, first side wall 430, and second side wall 432. As illustrated in FIGS. 12B-C, the second end section 416 can also include one or more tool engagement feature(s) 428, such as a notch, cut-out, or groove. Each tool-engagement feature 428 may be configured to engage an insertion tool (e.g., outer sleeve 202) as described further herein.

The second end section 416 of the body member 402 may be configured to engage the first and/or second endplates 408, 410. For example, the second end section 416 can include at least one recess, such as a groove, notch, and/or channel, configured to receive at least a portion of the first and/or second endplate 408, 410 therein. As illustrated in FIG. 12A, an upper portion of the second end section 416 can include two notches 446, 448, which may be configured to engage the first endplate 408. Those skilled in the art may appreciate that a lower portion of the second end section 416 can also include two notches configured to engage the second endplate 410.

As described herein, the first and/or second endplates 408, 410 may be configured to pivot relative to the body member 402. In some embodiments, the first and/or second endplates 408, 410 may be pivotably, jointedly, and/or hingedly coupled to the body member 402. Accordingly, the body member 402 may include one or more hinge elements. Each hinge element may be disposed on the second end section 416 of the body member 402. In some embodiments, the hinge element can include a recess, such as a bore, hole, aperture, and/or channel. In other embodiments, the hinge element can include a protrusion, such as a pin, axle, shaft, and/or rod. The hinge element may be rounded and/or curved. In some embodiments, the hinge element can be cylindrical or partially cylindrical. The hinge element can define an axis of rotation. The axis of rotation may be parallel to a horizontal transverse axis 438 of the expandable implant 400. As illustrated in FIGS. 12A-B, the body member 402 can include a first hinge element 434 and a second hinge element 436. In these embodiments, the first and second hinge elements 434, 436 may include, respectively, a first bore and a second bore. In some embodiments, the first hinge element 434 may be configured to form a joint with a corresponding hinge element on the first endplate 408 and the second hinge element 436 may be configured to form a joint with a corresponding hinge element on the second endplate 410. In other embodiments, the first hinge element 434 may be configured to engage the first endplate 408 and the second hinge element 436 may be configured to engage the second endplate 410. The body member 402 can include two, four, six, or more hinge elements. In some embodiments, the second end section 416 of the body member 402 can include a third hinge element 440 and a fourth hinge element 442, as illustrated in FIG. 12A. In some embodiments, the body member 402 can include two hinge elements (e.g., first and third hinge elements 434, 440) on the upper portion and two hinge elements (e.g., second and fourth hinge elements 436, 442) on the lower portion thereof. The first and third hinge elements 434, 440 may be configured to be coaxial with axis 510 of the first endplate 408 when in an assembled configuration. The second and fourth hinge elements 436, 442 may be configured to be coaxial with a corresponding axis of the second endplate 410. In other embodiments, the body member 402 can include two hinge elements (e.g., first and second hinge elements 434, 436) at the first side 429 and two hinge elements (e.g., third and fourth hinge elements 440, 442) at the second side 431.

In some embodiments where one or more hinge elements include a bore, the expandable spinal implant 400 can also include one or more proximal pivot pins 444, as illustrated in FIG. 11. As illustrated in FIG. 11, the expandable spinal implant 400 can include four pivot pins 444, wherein each pivot pin 444 corresponds to each of the hinge elements 434, 436, 440, and 442. Each pivot pin 444 can include a curved and/or rounded exterior surface. In some embodiments, each pivot pin 444 may be cylindrical. Each pivot pin 444 may be configured to be pivotably and/or rotatably received within the respective hinge element 434, 436, 440, and/or 442. Each pivot pin 444 may be configured to be coaxial with respect to the respective hinge element 434, 436, 440, and/or 442.

Figure 12D:
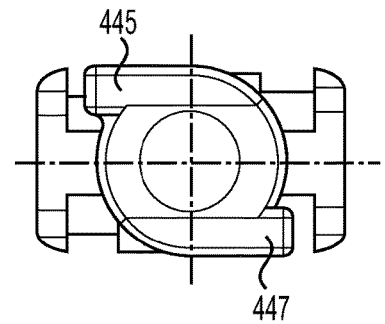
FIG. 12D illustrates an end view of one embodiment of a body member described herein.

The first end section 414 of the body member 402 may also be configured to engage the first and/or second endplates 408, 410. For example, the first end section 414 can include at least one extension members. As illustrated in FIG. 12D, the first end section 414 can include a first extension member 445 at an upper end thereof and configured to engage the first endplate 408. The first end section 414 can include a second extension member 447 at a lower end thereof and configured to engage the second endplate 410. The extension members 445, 447 may each be configured to fit within a corresponding groove on the first and/or second endplates 408, 410, for example, as illustrated in FIG. 16D.

The first driving unit 404 can be configured to engage the first endplate 408. The second driving unit 406 can be configured to engage the second endplate 410. In some embodiments, the first and/or second endplates 408, 410 may be configured to translate and/or slide relative to the first and/or second driving units 404, 406. When in an assembled configuration, the first and/or second driving units 404, 406 can be located distal to the body member 402 (e.g., closer to the first end 401 than the second end 403), as illustrated in FIG. 16A.

Figure 13A:
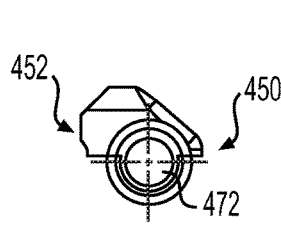
FIG. 13A illustrates a side view of one embodiment of a driving unit described herein.
Figure 13B:
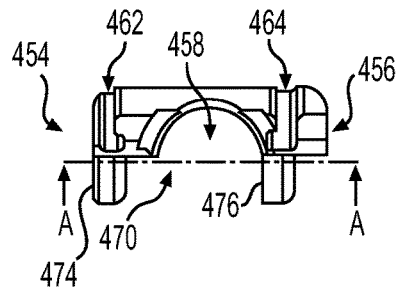
FIG. 13B illustrates an end view of one embodiment of a driving unit described herein.
Figure 13C:
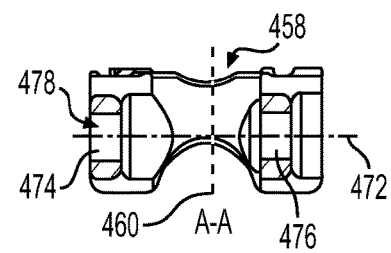
FIG. 13C illustrates a cross-sectional view of one embodiment of a driving unit described herein.

As illustrated in FIG. 13A, the first driving unit 404 can include a first (e.g., leading and/or distal) end 450 and a second (e.g., trailing and/or proximal) end 452. The first driving unit 404 can also include a first side 454 and a second side 456, as illustrated in FIG. 13B. The first driving unit 404 can include a width, as measured from the first side 454 to the second side 456, which is generally equal to a width of the body member 402. The first driving unit 404 can include a tapered section. The tapered section may be located at the first end 450. The tapered section can include a variable height. For example, as illustrated in FIG. 13A, at least a portion of the first driving unit 404 can have a height that decreases towards the first end 450. As illustrated in FIGS. 13B-C, the first driving unit 404 can include a channel 458 extending therethrough along longitudinal axis 460. As illustrated in FIGS. 13B-C, the channel 458 can include a curved opening. As described further herein, the channel 458 can be configured to receive at least a portion of the nut 516 of the actuator assembly 412 therein. In some embodiments, the nut 516 may be configured to nest within the channel 458. In other embodiments, the channel 458 may include a radius of curvature that is greater than or equal to a radius of curvature of the outer surface of the nut 516. When in an assembled configuration, the first driving unit 404 may be configured to pivot about the nut 516.

The first driving unit 404 can include one or more mating elements. In some embodiments, the first driving unit 404 can include two mating elements. The mating elements may be configured to engage the first endplate 408. As illustrated in FIG. 13B, the first driving unit 404 can include a first mating element 462 at the first side 454 and a second mating element 464 at the second side 456. The mating element(s) may be generally located at the second end 452 of the first driving unit 404.

Figure 13D:
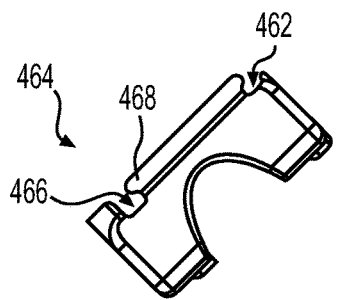
FIG. 13D illustrates an end view of one embodiment of a driving unit described herein.

Each mating element of the first driving unit 404 can be configured (e.g., shaped) to mate with a corresponding complementary mating element on the first endplate 408 as described herein. Each mating element can be ramped (e.g., angled, inclined, and/or declined), and/or can include a ramped member. In some embodiments, one or more mating elements on the first driving unit 404 can include a protrusion (e.g., a tongue, rail, and/or shoulder). In other embodiments, one or more mating elements on the first driving unit 404 can include a recess (e.g., a groove, track, and/or channel). In some embodiments, one or more mating elements can include an extension member. For example, as illustrated in FIG. 13D, second mating element 464 can include a groove 466 and an extension tab 468 that can at least partially protrude into the groove 466. Those skilled in the art may appreciate the groove 466 may be configured to receive an extension tab of a mating element of the first endplate 408 therein. Additionally, the tab 468 may provide enhanced engagement with the first endplate 408 thereby reducing movement, separation, and/or decoupling between the first endplate 408 and first driving unit 404 when in use. As illustrated in FIG. 13D, first mating element 462 may include a groove and a tab. In other embodiments, any and/or all mating elements of the first driving unit 404 can include a groove and a tab. In yet other embodiments, the mating element can include a protrusion and an engagement receptacle (e.g., a cut-out) that overlaps the protrusion.

Figure 13E:
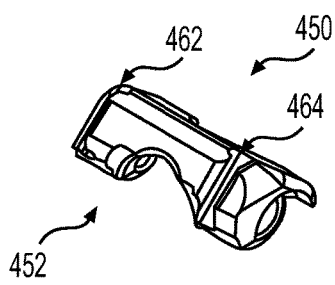
FIGS. 13E-F illustrate perspective views of one embodiment of a driving unit described herein.
Figure 13F:
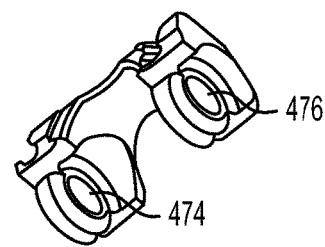

Each mating element on the first driving unit 404 may include an inclination substantially similar to that of each complementary mating element on the first endplate 408. In some embodiments, each mating element on the first driving unit 404 can be inclined longitudinally from the second end 452 towards the first end 450, as illustrated in FIG. 13E. In other embodiments, each mating element on the first driving unit 404 may be angled relative to the longitudinal axis 460, e.g., towards the first end 450.

As described herein, the first and second driving units 404, 406 may be configured to pivot relative to each other. In some embodiments, the first and second driving units 404, 406 may be pivotably, jointedly, and/or hingedly coupled to each other. In other embodiments, the first and/or second driving units 404, 406 may be configured to pivot about the nut 516 of the actuator assembly 412. Accordingly, the first driving unit 404 can include one or more hinge elements. As illustrated in FIGS. 13C and 13E, the first driving unit 404 can include a first hinge element 474 and a second hinge element 476. Each hinge element may extend from an inner side 470 of the first driving unit 404, as illustrated in FIG. 13B. The one or more hinge elements may be located on the first and/or second sides 454, 456 of the first driving unit 404. In some embodiments, the hinge element can include a recess, such as a bore, hole, aperture, and/or channel. In other embodiments, the hinge element can include a protrusion, such as a pin, axle, shaft, and/or rod. The hinge element may be rounded and/or curved. In some embodiments, the hinge element can be cylindrical or partially cylindrical. The hinge element can define an axis of rotation 472, as illustrated in FIG. 13C. The axis of rotation may be parallel to the horizontal transverse axis 438 of the expandable implant 400. In some embodiments, all of the hinge elements on the first driving unit 404 may be coaxial. As illustrated in FIG. 13C, the first and second hinge elements 474, 476 may include, respectively, a first bore and a second bore. The first and second bores may be coaxial along axis 472. The first and second bores may define a transverse channel 478 through the first driving unit 404. The first and second hinge elements 474, 476 may be configured to form a joint with corresponding hinge elements on the second driving element 406. As illustrated in FIG. 13C, the first hinge element 474 can be located at the first side 454 and the second hinge element 476 can be located at the second side 456. In some embodiments, the first hinge element 474 may be located directly on the first side 454 and the second hinge element 476 may be inset from the second side 456, as illustrated in FIG. 13C. In other embodiments, the first hinge element 474 may be inset from the first side 454 and the second hinge element 476 can be located directly on the second side 456. Those skilled in the art may appreciate that in use, the staggered and/or offset hinge elements can enable the first driving unit 404 to nest and/or mesh with the second driving unit 406.

The second driving unit 406 may be configured to engage the second endplate 410. In use, the expandable spinal implant 400 may be oriented such that the first driving unit 404 is the top, upper, and/or superior driving unit and the second driving unit 406 is the bottom, lower, and/or inferior driving unit. The second driving unit 406 may include some or all of the same features as the first driving unit 404. In some embodiments, the second driving unit 406 may be identical to the first driving unit 404. Those skilled in the art may appreciate that the description of the first driving unit 404 herein may be applied to the second driving unit 406 unless stated otherwise. The second driving unit 406 may include one or more mating elements that may be configured to engage one or more complementary mating elements on the second endplate 410. When in an assembled configuration, the mating elements on the second driving unit 406 may diverge from the mating elements on the first driving unit 404 along a longitudinal axis from a position relatively adjacent to the second end 403 of the implant 400 to a position relatively adjacent to the first end 401 thereof. In other embodiments, each mating element on the second driving unit 406 can be declined towards the first end 401 of the implant 400.

The second driving unit 406 may be configured to pivot relative to the first driving unit 404. As illustrated in FIG. 11, the second driving unit 406 can include a first hinge element 482 and a second hinge element 484. The first and second hinge elements 482, 484 may each include a first and second bore, respectively. When in an assembled configuration, the first and second hinge elements 482, 484 of the second driving unit 406 may be coaxial with the first and second hinge elements 474, 476 of the first driving unit 404 and/or the axis of rotation 472.

In some embodiments where one or more hinge elements of the first and/or second driving units 404, 406 include a bore, the expandable spinal implant 400 can also include one or more distal pivot pins. As illustrated in FIG. 11, the expandable spinal implant 400 can include a first distal pivot pin 480 and a second distal pivot pin 481. Each pivot pin 480, 481 can include a curved and/or rounded exterior surface. In some embodiments, each pivot pin 480, 481 may be cylindrical. Each pivot pin 480, 481 may be configured to be pivotably and/or rotatably received within the respective hinge element(s) of the first and/or second driving units 404, 406. For example, the first pivot pin 480 may be configured to be pivotably and/or rotatably received within hinge elements 474, 482. The second pivot pin 481 may be configured to be pivotably and/or rotatably received within hinge elements 476, 484. Each pivot pin 480, 481 may also be configured to be at least partially received within the nut 516 of the actuator assembly 412, described further herein. In some embodiments, each pivot pin 480, 481 may be pivotably and/or rotatably received within the nut 516. In some embodiments, the pivot pins 480, 481 may couple the first and second driving units 404, 406 with the nut 516.

The first and/or second endplates 408, 410 may be configured to engage the body member 402. The first endplate 408 may be configured to engage the first driving unit 404 and the second endplate 410 may be configured to engage the second driving unit 406. In use, the expandable implant 400 may be oriented such that the first endplate 408 is the top, superior, and/or upper endplate and the second endplate 410 is the bottom, inferior, and/or lower endplate. First endplate 408 and second endplate 410 may include some or all of the same features. Those skilled in the art may appreciate that the description of the first endplate 408 herein may be applied to the second endplate 410 unless stated otherwise. For example, any description of the relationship between the first endplate 408 and the first driving unit 404 may be applied to the second endplate 410 and the second driving unit 406.

Figure 14A:
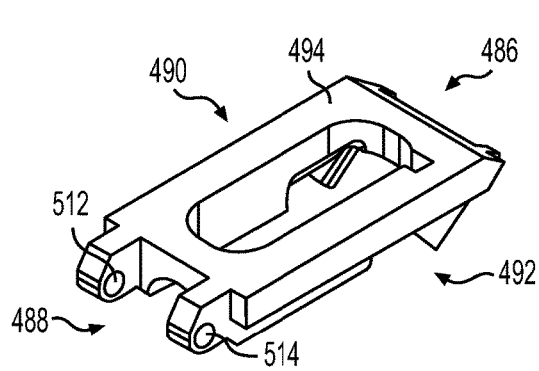
FIGS. 14A-B illustrate perspective views of one embodiment of an endplate described herein.
Figure 14B:
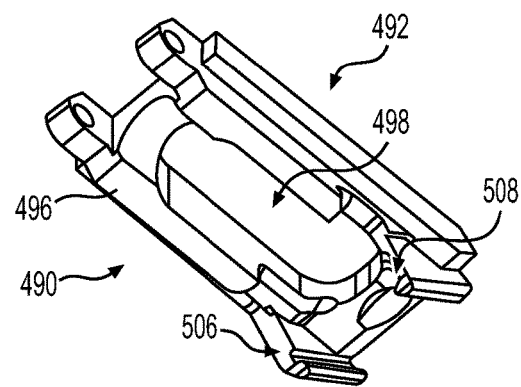
Figure 14C:
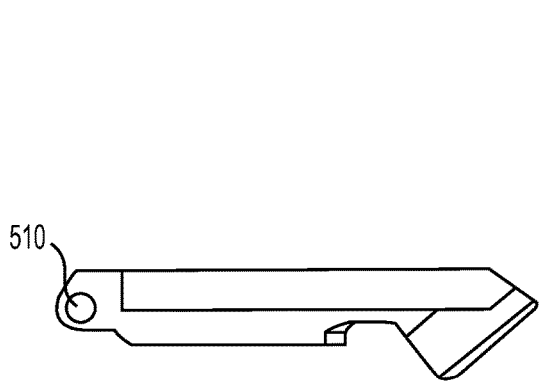
FIG. 14C illustrates a side view of one embodiment of an endplate described herein.
Figure 14D:
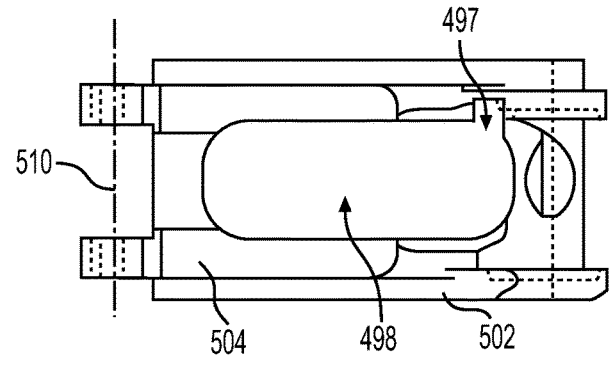
FIG. 14D illustrates an inner view of one embodiment of an endplate described herein.
Figure 14E:
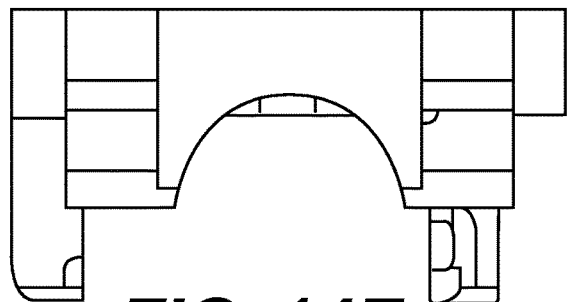
FIG. 14E illustrates an end view of one embodiment of an endplate described herein.

First endplate 408 can be configured to pivot relative to the body member 402. In some embodiments, the first endplate 408 can be configured to form a joint with the body member 402. First endplate 408 may also be configured to slideably engage the first driving unit 404. As illustrated in FIG. 14A, the first endplate 408 can include a first (e.g., leading and/or distal) end 486, a second (e.g., trailing and/or proximal) end 488, a first side 490, and a second side 492. The first endplate 408 can include a length between the first and second ends 486, 488 and a width between the first and second sides 490, 492. The first endplate 408 can include a third (e.g., outer) side 494, illustrated in FIG. 14A, and a fourth (e.g., inner) side 496, illustrated in FIG. 14B. As illustrated in FIG. 14B, the first endplate 408 can also include a through-hole 498 that passes from the outer side 494 to the inner side 496. The through-hole 498 can be configured to enable bone graft material deposited within the expandable implant 400 to engage, contact, and/or fuse with an adjacent vertebral body. As illustrated in FIG. 14D, the first endplate 408 can include a cut-out or groove 497, which may be in fluid communication with the through-hole 498. The groove 497 may be configured to receive a portion of the body member 402 therein (e.g., extension member 445), as illustrated in FIG. 16D. The outer side 494 may be configured to engage a vertebral body. The outer side 494 may be referred to as an outer surface and/or a superior surface. In some embodiments, the outer side 494 can include a plurality of protrusions (e.g., bumps, teeth, and/or peaks) configured to retain the implant 400 within an intervertebral space. The outer side 494 can be generally planar, concave, and/or convex.

In some embodiments, inner side 496 can include at least one wall segment extending therefrom. Each wall segment may extend partially or completely along the length of the first endplate 408. As illustrated in FIG. 14B, the first side 490 can include at least one wall segment and the second side 492 can include at least one wall segment. In some embodiments, the first side and/or the second side can include a plurality of overlapping and/or staggered wall segments. The wall segments may be staggered along the length and/or the width of the first endplate 408. In some embodiments, the wall segments may be separated by a gap. For example, as illustrated in FIG. 14D, the first side 490 can include an outer wall segment 502 and an inner wall segment 504. The overlapping and/or staggered wall segments can advantageously enable the first and second endplates 408, 410 to overlap, thereby reducing the height of the expandable implant 400 when in a collapsed configuration, for example, as illustrated in FIGS. 16A-D.

The first endplate 408 can include one or more mating elements. The one or more mating elements may be located at the first end 486. In some embodiments, one or more mating elements of the first endplate 408 can include a protrusion (e.g., a tongue, rail, and/or shoulder). In other embodiments, one or more mating elements of the first endplate 408 can include a recess (e.g., a groove, track, and/or channel). In some embodiments, at least one mating element can include an extension member. For example, at least one of the mating elements can a groove and an extension tab that can at least partially protrude into the groove. As another example, the mating element can include a protrusion and an engagement receptacle that overlaps the protrusion. The mating elements on the first endplate 408 can be configured to form a slidable joint with a complementary mating element on the first driving unit 404. Accordingly, the first driving unit 404 may be configured to slideably engage the first endplate 408. The slideable joint may advantageously enable the expandable implant 400 to transition reversibly between expanded and contracted configurations. The slidable joint may include, for example, a tabled splice joint, a dovetail joint, a tongue and groove joint, or another suitable joint. In some embodiments, one or more mating elements on the first endplate 404 can include a recess (e.g., a groove, track, and/or channel), and one or more mating elements on the first driving unit 404 can include a protrusion (e.g., a tongue, rail, and/or shoulder) configured to slide within the groove. In other embodiments, one or more mating elements on the first endplate 408 can include a protrusion and one or more mating elements on the first driving unit 404 can include a recess.

In some embodiments, the mating elements may be located on and/or extend from the inner side 496. In some embodiments, at least one mating element may be located on a wall segment. In other embodiments, the first side 490 can include at least one mating element and the second side 492 can include at least one mating element. As illustrated in FIG. 14B, the first endplate 404 can include a first mating element 506 and a second mating element 508. The first mating element 506 may be located at the first side 490 and the second mating element 508 may be located at the second side 492. The first and second mating elements 506, 508 may each be configured to engage a complementary mating element on the first driving unit 404. Those skilled in the art may appreciate that first and second mating elements on the second endplate 410 may each be configured to engage a complementary mating element on the second driving unit 406. Accordingly, each mating element can be ramped (e.g., angled, inclined, and/or declined), and/or can include a ramped member. The mating elements on the first endplate 404 may have substantially similar inclinations, when in an assembled configuration, as their complementary mating elements on the first driving unit 404. As illustrated in FIG. 14B, the first and second mating elements 506, 508 may be angled (e.g., inclined or declined) away from the outer side 494 in a direction from the first end 486 towards the second end 488. For example, the first and/or second mating elements 506, 508 may be inclined longitudinally in a direction from the second end 488 towards the first end 486.

The first and/or second endplate 408, 410 may be configured to be pivotably coupled to the second end section 416 of the body member 402. In some embodiments, the first endplate 408 may be configured to pivot about a first pivot point (e.g., axis 510, described herein), and the second endplate 410 may be configured to pivot about a second pivot point (e.g., axis 546, described herein) that is different from the first pivot point. The first endplate 408 can include one or more hinge elements. The one or more hinge elements may be located at the second end 488. In some embodiments, the first endplate 408 can include at least one hinge element at the first side 490 and at least one hinge element at the second side 492. As described herein, the hinge element(s) may be configured to enable the first and/or second endplates 408, 410 to pivot relative to the body member 402. In some embodiments, the hinge element can include a recess, such as a bore, hole, aperture, and/or channel. In other embodiments, the hinge element can include a protrusion, such as a pin, axle, shaft, and/or rod. The hinge element may be rounded and/or curved. In some embodiments, the hinge element can be cylindrical or partially cylindrical. As illustrated in FIGS. 14C-D, the hinge element can define an axis of rotation 510. The axis of rotation 510 may be parallel to the horizontal transverse axis 438 of the expandable implant 400, described herein with respect to the body member 402. As illustrated in FIG. 14A, the first endplate 408 can include a first hinge element 512 and a second hinge element 514. In these embodiments, the first and second hinge elements 512, 514 may include, respectively, a first bore and a second bore. The first and second hinge elements 512, 514 (e.g., the first and second bores) may be coaxial with the axis 510. In some embodiments, the first and second hinge elements 512, 514 may be configured to form a joint with corresponding hinge elements on the body member 402 (e.g., first and third hinge elements 434, 440). The hinge elements 512, 514, 434, and 440 may be configured to be coaxial when the implant 400 is in an assembled configuration. Those skilled in the art may appreciate that the second endplate 410 can include first and second hinge elements configured to form a joint with corresponding hinge elements on the body member 402 (e.g., second and fourth hinge elements 436, 442). The hinge elements of the second endplate 410 and the hinge elements 436, 442 may be configured to be coaxial when the implant 400 is in an assembled configuration. Additionally, those skilled in the art may appreciate that when a hinge element includes a bore, the bore may be configured to pivotably and/or rotatably receive proximal pivot pin 444 therein.

Figure 15A:
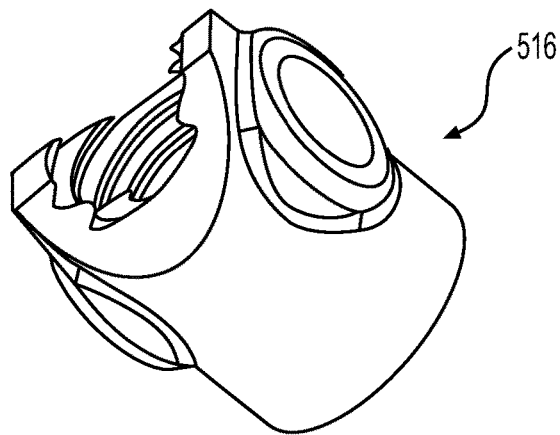
FIGS. 15A-B illustrate perspective views of one embodiment of a nut described herein.
Figure 15B:
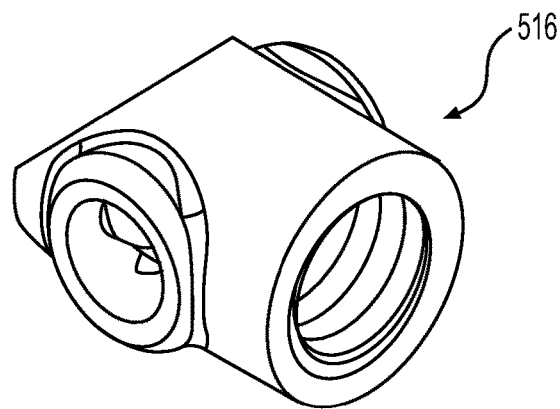
Figure 15C:
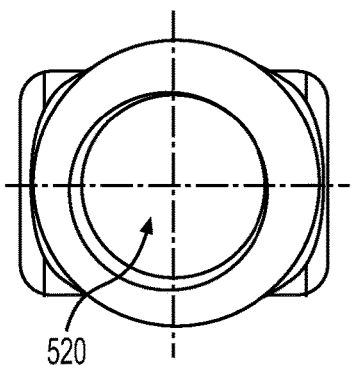
FIG. 15C illustrates an end view of one embodiment of a nut described herein.
Figure 15D:
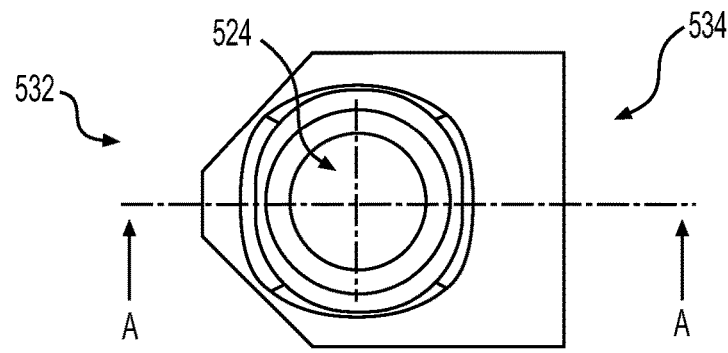
FIG. 15D illustrates a side view of one embodiment of a nut described herein.
Figure 15E:
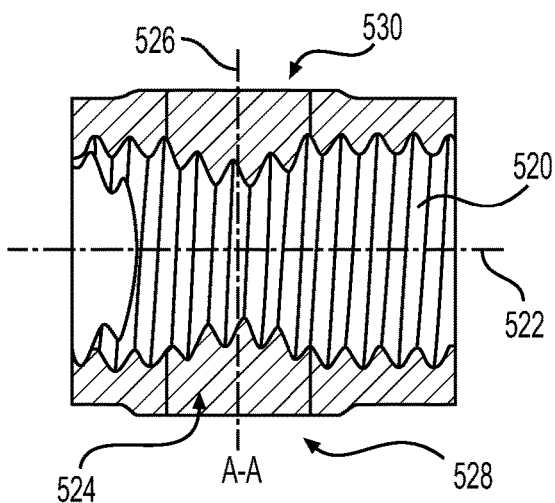
FIG. 15E illustrates a cross-sectional view of one embodiment of a nut described herein.

As illustrated in FIG. 11, the actuator assembly 412 can include a nut 516 and an actuation screw 518. In some embodiments, the actuator assembly 412 can also include a snap ring (not shown) and/or a washer (not shown). The nut 516 can be configured to be received at least partially within the first driving unit 404 and/or the second driving unit 406. For example, the nut 516 may be configured to be at least partially received within the channel 458 of the first driving unit 404 and/or a channel of the second driving unit 406. As illustrated in FIGS. 15A-C, the nut 516 can include a generally curved and/or cylindrical outer surface. The outer surface may have a radius of curvature that is less than or equal to the radius of curvature of the channel(s). As illustrated in FIG. 15D, the nut 516 can include a first (e.g., leading and/or distal) end 532 and a second (e.g., trailing and/or proximal) end 534. The first end 532 can be tapered. As illustrated in FIGS. 15C and 15E, the nut 516 can include a longitudinal bore 520 that extends along a longitudinal axis 522. The bore 520 may be internally-threaded. The nut 516 may also include a transverse bore 524 that extends along transverse axis 526, as illustrated in FIGS. 15D-E. The transverse bore 524 may be in fluid communication with the longitudinal bore 520. In some embodiments, the transverse bore 524 can be perpendicular to the longitudinal bore 520. The transverse bore 524 may be non-threaded (e.g., smooth). In some embodiments, the transverse bore 524 can extend entirely through the nut 516. As illustrated in FIG. 15E, the transverse bore 524 can include a first opening 528 and a second opening 530. In other embodiments, the nut 516 can include two transverse bores and/or depressions extending partially therethrough. When in an assembled configuration, the transverse bore 524 may be configured to be coaxial with one or more hinge elements of the first and second driving units 404, 406. The transverse bore 524 may be configured to receive at least a portion of the distal pivot pins 480, 481 therein. For example, the transverse bore 524 may have a diameter that is greater than or equal to a diameter of the pivot pins 480, 481. In some embodiments, the pivot pin 480 may be received through the first opening 528 and the pivot pin 481 may be received through the second opening 530.

As illustrated in FIG. 11, the actuation screw 518 can include a head 536 and a threaded body 538. The head 536 can be configured to be completely contained between the first and second endplates 408, 410 when the expandable spinal implant 400 is in an assembled configuration. The head 536 may be configured to engage the first end section 414 of the body member 402. For example, the head 536 can be configured to be received within the first bore 418 of the body member 402. In some embodiments, the head 536 can include a diameter that is greater than a diameter of the reduced-diameter section 426 of the first bore. The threaded body 538 can include an outer diameter that is less than the diameter of the reduced-diameter section 426. The threaded body 538 can be configured to engage the nut 516. For example, the threaded body 538 may be configured to threadably engage the longitudinal bore 520 of the nut 516. The head 536 can include a tool-engagement feature, such as a recess or socket. The tool-engagement feature may be configured to engage a driver as described herein.

As illustrated in FIG. 11, the head 536 can include a circumferential groove 540. The circumferential groove 540 can be configured to receive the snap ring therein. The circumferential groove 540 of the actuation screw 518 may be longitudinally aligned with the circumferential groove 424 of the body member 402. Accordingly, both circumferential grooves 424, 540 may be configured to receive at least a portion of the snap ring therein. Those skilled in the art may appreciate that in use, the snap ring may advantageously retain the actuation screw 518 within the body member 402. The washer may have an outer diameter generally less than or equal to the diameter of the first bore 418, and may have an inner diameter generally greater than or equal to the diameter of the reduced-diameter section 426 of the first bore 418. The washer may be configured to receive the threaded body 538 of the actuation screw 518 therethrough. The washer may be configured to be received within the first bore 418 of the body member 402. In use, the washer may be positioned between the head 536 of the actuation screw 518 and the body member 402, and may advantageously provide a bearing surface for the actuation screw 518.

In use, the expandable spinal implant 400 may advantageously be configured to reversibly transition between a collapsed configuration and an expanded configuration. The height and/or lordotic angle of the spinal implant 400 may vary between the collapsed and expanded configurations. In the collapsed configuration, for example, as illustrated in FIGS. 16A-B, the expandable spinal implant 400 can include a first height $H_i$ (e.g., measured as the greatest distance between the outer surface 494 of the first endplate 408 and an outer surface 542 of the second endplate 410). In these embodiments, the implant 400 may be wedge-shaped when viewed from a first and/or second side 405, 407 (e.g., as illustrated in FIG. 16A). For example, the first end 401 may be taller than the second end 403, or vice versa. In other embodiments, the first and second endplates 408, 410 may be generally parallel when in the collapsed configuration. In these embodiments, the height of the implant 400 at the first and second ends 401, 403 may be generally equal. In yet other embodiments, the implant 400 may be wedge-shaped when viewed from the first and/or second end 401, 403, as illustrated in FIG. 16B. For example, the second side 407 may be taller than the first side 405, or vice versa.

Figure 17A:
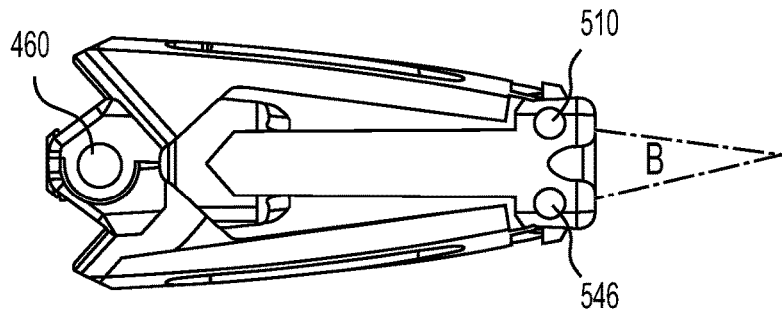
FIG. 17A illustrates a side view of one embodiment of an expandable spinal implant in an expanded configuration described herein.
Figure 17B:
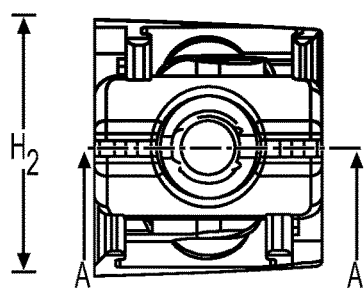
FIG. 17B illustrates an end view of one embodiment of an expandable spinal implant in an expanded configuration described herein.

In the expanded configuration, for example, as illustrated in FIG. 17B, the expandable spinal implant 400 can include a second height, $H_2$, that is greater than the first height. In some embodiments, the second height can be from about 25% to about 200% greater than the first height. In other embodiments, the second height can be from about 100% to about 150% greater than the first height. In some embodiments, the first height can be in the range of from about 5 mm to about 10 mm, and/or the second height can be in the range of from about 15 mm to about 20 mm. The change in height can be caused by movement of the first and second endplates 408, 410 towards and/or away from each other and/or the body member 402. As described herein, the first endplate 408 may be configured to pivot relative to the body member 402 about axis 510. The second endplate 410 may be configured to pivot relative to the body member 402 about axis 546, illustrated in FIG. 17A. Accordingly, the first ends 486, 544 of the first and second endplates 408, 410 may be pivoted towards and/or away from each other and/or the body member 402. In some embodiments, the first ends 486, 544 of the first and second endplates 408, 410 can be separated by a first distance when in the collapsed configuration and a second distance when in the expanded configuration, wherein the second distance is greater than the first distance. When in an expanded configuration, the expandable spinal implant 400 may be wedge-shaped when viewed from the first and/or second side 405, 407, as illustrated in FIG. 17A, and/or when viewed from the first and/or second end 401, 403, as illustrated in FIG. 17B. Advantageously, this shape can enhance contact between the implant 400 and vertebral endplates, thereby encouraging a secure fit within an intervertebral space.

In some embodiments, the first and second endplates 408, 410 can define a first angle along a longitudinal axis 511 when in the collapsed configuration. In other embodiments, the first and second endplates 408, 410 may be generally parallel to each other when in the collapsed configuration. As illustrated in FIG. 17A, the first and second endplates 408, 410 can define a second angle β along the longitudinal axis 511, when in the expanded configuration. The first and/or second endplates 408, 410 can pivot apart about the respective axes 510, 546 to expand the implant 400 and orient the first and second endplates 408, 410 at the second angle β. The second angle β may thus be greater than the first angle. In some embodiments, the first (e.g., collapsed) angle can be in the range of from about 1° to about 20°. In other embodiments, the first angle may be in the range of from about 10° to about 20°. In some embodiments, the second (e.g., expanded) angle β can be in the range of from about 10° to about 40°. In other embodiments, the second angle β may be in the range of from about 15° to about 30°. In some embodiments, the implant 400 may be expanded by both the linear and pivotal movement of the first and/or second endplates 408, 410. Those skilled in the art may appreciate that, in use, the height and/or lordotic angle of the expandable spinal implant 400 can advantageously be adjusted to accommodate an individual patient's anatomy. Additionally, the expandable spinal implant 400 may be inserted into an intervertebral space in the collapsed configuration, which may entail less trauma to surrounding tissue due to its smaller size.

Embodiments herein are also directed to methods of installing the expandable spinal implant 400. Methods can include providing the expandable spinal implant 400 in the collapsed configuration as described herein. Methods can also include coupling the expandable spinal implant 400 with inserter 200. This step can include inserting the countertorque tab(s) 214 of the inserter 200 into the tool-engagement feature(s) 428 of the body member 402. This step can also include threading the first end 210 of the inner sleeve 204 of the inserter 200 into the second bore 420 of the body member 402. Those skilled in the art may appreciate that in other embodiments, the spinal implant 400 may be installed without the use of the inserter 200.

In some embodiments, the method can also include inserting the expandable spinal implant 400 between two adjacent vertebrae. Those skilled in the art may appreciate that the first ends of the first and second driving units 404, 406 may define the leading end of the implant 400. Accordingly, the tapered first end of the first and second driving units 404, 406 may advantageously be used to distract the adjacent vertebrae. As described herein, the expandable spinal implant 400 may be inserted anywhere along the spinal column, such as between lumbar, thoracic, and/or cervical vertebrae. In addition, the expandable spinal implant 400 may be inserted along any approach, such as transforaminal, posterior, lateral, and/or anterior. In some embodiments, the implant 400 may be inserted using minimally invasive methods. In some embodiments, the intervertebral space may be prepared beforehand, for example, by performing a discectomy to remove some or all of the intervertebral disc.

Figure 17C:
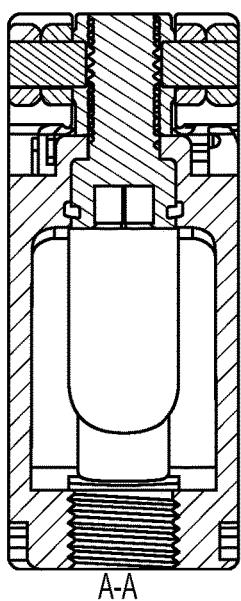
FIG. 17C illustrates a cross-sectional view of one embodiment of an expandable spinal implant in an expanded configuration described herein.
Figure 17D:
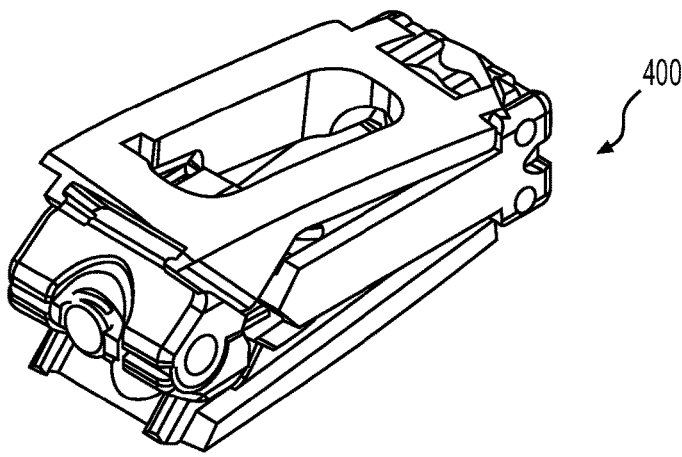
FIG. 17D illustrates a perspective view of one embodiment of an expandable spinal implant in an expanded configuration described herein.

The method can also include expanding the expandable implant 400, for example, by transitioning the implant 400 from the collapsed configuration to the expanded configuration. To expand the implant 400, the first and second driving units 404, 406 may be moved towards the body member 402, or vice versa, as illustrated in FIGS. 16C and 17C. This step can include urging a driver into engagement with the actuation screw 518. In some embodiments, this step can include inserting driver 206 through the inner sleeve 204 and/or the body member 402 and into engagement with the actuation screw 518. In these embodiments, the inner sleeve 204 may be coupled with the expandable implant 400 prior to engaging the driver 206 with the actuation screw 518. For example, the first end 210 of the inner sleeve 204 may threadably engage the second bore 420 of the body member 402.

Once the driver is engaged with the actuation screw 518, the step of expanding the implant 400 can also include applying a rotational force to the driver 206 to rotate the actuation screw 518. As the actuation screw 518 rotates in a first direction, the threaded body 538 engages the nut 516, translating the nut 516 relative to the body member 402. The proximal pivot pins 480, 481 may pivotably couple the nut 516, first driving unit 404, and second driving unit 406. Thus, as the nut 516 translates, it may urge the first and/or second driving units 404, 406 to translate and/or pivot. As the body member 402 and the driving units 404, 406 translate towards each other and/or pivot, the respective mating elements of the driving units 404, 406 may push against complementary mating elements on the first and second endplates 408, 410 thereby pushing the first ends 486, 544 of the first and second endplates 408, 410 apart and increasing the height of the implant 400. Because the second ends of the first and second endplates 408, 410 may be pivotably coupled to the body member 402, the first ends 486, 544 may pivot apart, thereby increasing and/or changing the angle between (e.g., defined by) the first and second endplates 408, 410. In other embodiments, as the actuation screw 518 is rotated in a second direction, the threaded body 538 may push the first and second driving units 404, 406 away from the body member 402, or vice versa. Thus, those skilled in the art may appreciate that the implant 400 may be reversibly expandable and/or collapsible. Accordingly, some embodiments can include reducing and/or adjusting the height of the implant 400, for example, by bringing the first and second endplates 408, 410 together. In some embodiments, the implant 400 can include a locking member configured to lock the implant in the collapsed and/or expanded configuration. In these embodiments, the method can also include the step of locking the implant 400 at a particular height.

After the expandable implant 400 has been expanded, the driver 206 may be removed (e.g., may be pulled proximally through the cannula of the inner sleeve 204). Bone graft material may then be inserted into the cavity 418 of the body member 402. In some embodiments, the bone graft material may be inserted through the cannula of the inner sleeve 204 to the cavity 418. Advantageously, the implant 400 may be backfilled with bone graft material in situ, rather than being prepacked prior to insertion. Accordingly, more bone graft material can be inserted, thereby promoting increased fusion. Additionally, the same cannula (e.g, of the inner sleeve 204) may be used to insert the driver 206 and the bone graft material. Advantageously, this method may save time and/or materials as compared to other methods that rely on separate instruments for insertion (and/or expansion) of the implant and subsequent insertion of bone graft material.

In some embodiments, any of the implants and instruments described above can be used with additional implants and instruments. In some embodiments, the implants and instruments can be used with stabilization members, such as plates, screws, and rods. In addition, a multi-level construct can be formed, wherein any one of the implants described above can be used on one level, while a similar or different implant (e.g., fusion or prosthetic) can be used on a different level.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A method of installing an expandable spinal implant, said method comprising:
    providing the expandable spinal implant, the expandable spinal implant including:
        a body member comprising a first end, a second end, and a cavity therebetween, the first end comprising a first bore and the second end comprising a second bore;
        a driving member comprising a threaded bore and a tapered outer surface;
        a first endplate configured to engage the body member and the driving member;
        a second endplate configured to engage the body member and the driving member; and
        an actuator assembly comprising an actuation screw, the actuation screw comprising a head and a threaded body; and
    coupling the expandable spinal implant to an inserter, the inserter configured to reversibly engage the body member, the inserter including a driver configured to be received within the body member and comprising an insertion portion having a length that is equal to at least 35% of a length of the expandable spinal implant; and
    inserting the expandable spinal implant between adjacent vertebral bodies in a collapsed position,
    wherein the inserter further comprises:
        an outer sleeve comprising a first end configured to engage the body member of the expandable spinal implant; and
        an inner sleeve comprising exterior threads at a first end thereof.

2. The method of claim 1, wherein the outer sleeve comprises at least one countertorque tab extending from a first end thereof.

3. The method of claim 1, wherein the inner sleeve is configured to be rotatably received within the outer sleeve.

4. The method of claim 1, wherein the driver is configured to be rotatably received within the inner sleeve.

5. The method of claim 1, wherein the length of the insertion portion of the driver is equal to at least 50% of the length of the expandable spinal implant.

6. The method of claim 1, wherein the first and second bores define an elongate channel extending longitudinally through the body member.

7. The method of claim 6, wherein the threaded body of the actuation screw is configured to threadably engage the threaded bore of the driving member.

8. The method of claim 1, wherein the first and second bores are coaxial.

9. The method of claim 1, wherein the first bore is non-threaded.

10. The method of claim 1, wherein the second bore is threaded.

11. The method of claim 1, wherein the second bore is configured to receive bone graft material therethrough.

12. The method of claim 1, wherein the threaded bore extends longitudinally through the driving member.

13. The method of claim 1, wherein the threaded body of the actuation screw is configured to engage the driving member.

14. A method of installing an expandable spinal implant, said method comprising:
    providing the expandable spinal implant in a collapsed position, the expandable spinal implant including:
        a body member comprising a first end section, a second end section, and a cavity therebetween, the first end section comprising a first bore and the second end section comprising a second bore;
        a driving member comprising a threaded bore and a tapered outer surface;
        a first endplate configured to engage the body member and the driving member;
        a second endplate configured to engage the body member and the driving member; and
        an actuator assembly comprising an actuation screw, the actuation screw comprising a head and a threaded body, wherein the head is configured to engage the first end section of the body member and the threaded body is configured to engage the threaded bore of the driving member;
    coupling the expandable spinal implant to an inserter, the inserter configured to reversibly engage the body member, the inserter comprising a driver configured to be received within the body member and comprising an insertion portion having a length that is equal to at least 35% of a length of the expandable spinal implant;
    inserting the expandable spinal implant between adjacent vertebral bodies; and
    expanding the expandable spinal implant from the collapsed position to an expanded position,
    wherein the inserter further comprises:
        an outer sleeve comprising a first end configured to engage the body member of the expandable spinal implant; and
        an inner sleeve comprising exterior threads at a first end thereof.

15. The method of claim 14, wherein the first end section of the body member comprises a first mating element configured to engage the first endplate and a second mating element configured to engage the second endplate.

16. The method of claim 14, wherein the second end section of the body member comprises a first mating element configured to engage the first endplate and a second mating element configured to engage the second endplate.

17. The method of claim 14, wherein the tapered outer surface of the driving member is located at a first end thereof.

18. The method of claim 17, wherein the driving member further comprises a second end, the second end comprising a first mating element configured to engage the first endplate and a second mating element configured to engage the second endplate.

* * * * *